United States Patent [19]

Humphrey

[11] 4,420,228
[45] Dec. 13, 1983

[54] METHOD AND APPARATUS FOR ANALYSIS OF CORNEAL SHAPE

[75] Inventor: William E. Humphrey, San Leandro, Calif.

[73] Assignee: Humphrey Instruments, Inc., San Leandro, Calif.

[21] Appl. No.: 163,663

[22] Filed: Jun. 27, 1980

Related U.S. Application Data

[63] Continuation-in-part of Ser. No. 158,849, Jun. 12, 1980.

[51] Int. Cl.³ .............................................. A61B 3/10
[52] U.S. Cl. ..................................... 351/212; 351/247
[58] Field of Search ................. 351/6, 13, 16, 40, 205, 351/211, 212, 221, 247

[56] References Cited

U.S. PATENT DOCUMENTS

| | | | |
|---|---|---|---|
| 3,453,437 | 7/1969 | Westheimer et al. | 351/6 |
| 3,781,096 | 12/1973 | Townsley | 351/16 |
| 4,019,813 | 4/1977 | Cornsweet et al. | 351/6 |
| 4,182,572 | 1/1980 | Humphrey | 356/127 |
| 4,199,816 | 4/1980 | Humphrey | 356/127 |

Primary Examiner—R. A. Rosenberger
Attorney, Agent, or Firm—Townsend and Townsend

[57] ABSTRACT

An analysis of the corneal shape through the combination of several keratometer measurements is disclosed. The eye is preferably scanned to a nasal angular position, a central angular position and a temporal angular position. The central position is straight ahead along the patient's line of sight. The temporal and nasal positions are in the broad range of up to 5° to 22°; the intermediate range of 10 to 15°; and the narrow range of 12° to 14° on either side. Measurements in sphere, cylinder and axes are taken. Astigmatism is in the more preferable format of 0°–90° astigmatism and 45°–135° astigmatism. When each individual point is measured with its respective estimate for sphere and cylinder components, these measurements are fitted to an idealized parameter. Then the three sets of curvature measurements taken at the specified locations are reduced to a set of adjusted, idealized curvatures all fitted to an elliptical model. Thereafter, these fitted values create final corneal shaped parameters, the particular process here including the creation of intermediate parameters. Finally, readings of central "k", corneal shape, apex position, cap size, vault height, corrected central "k" and goodness of fit are all set forth.

5 Claims, 22 Drawing Figures

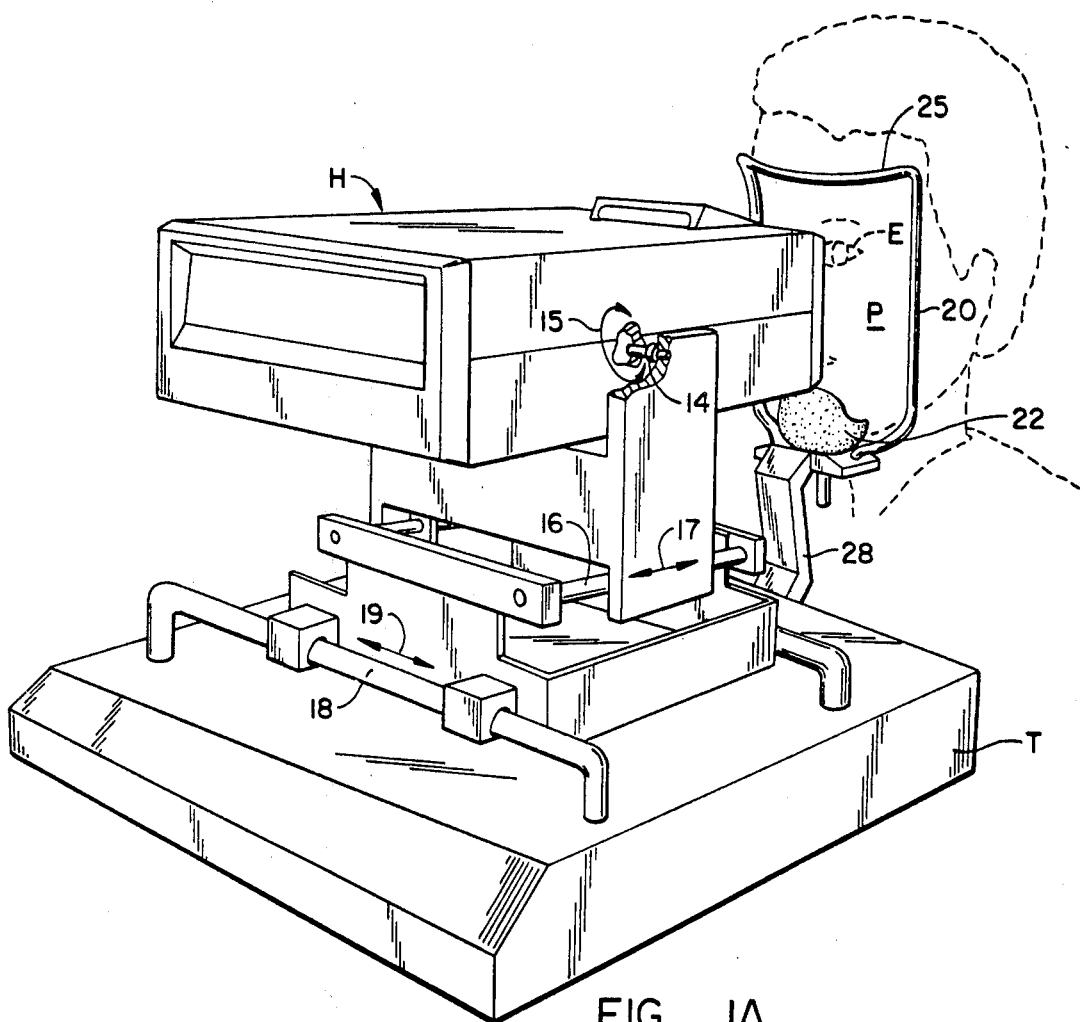
FIG._1A.
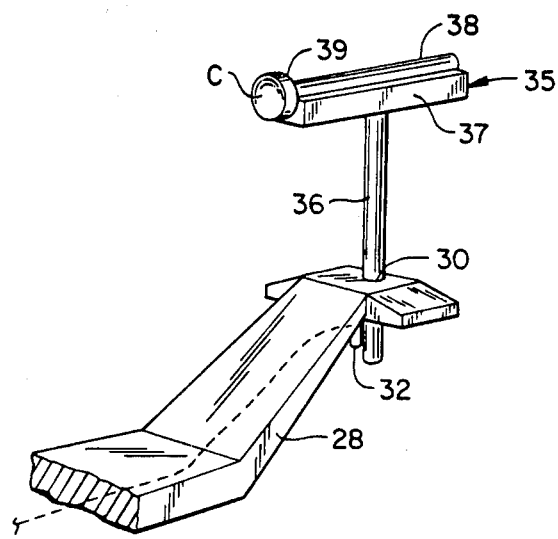
FIG._1B.

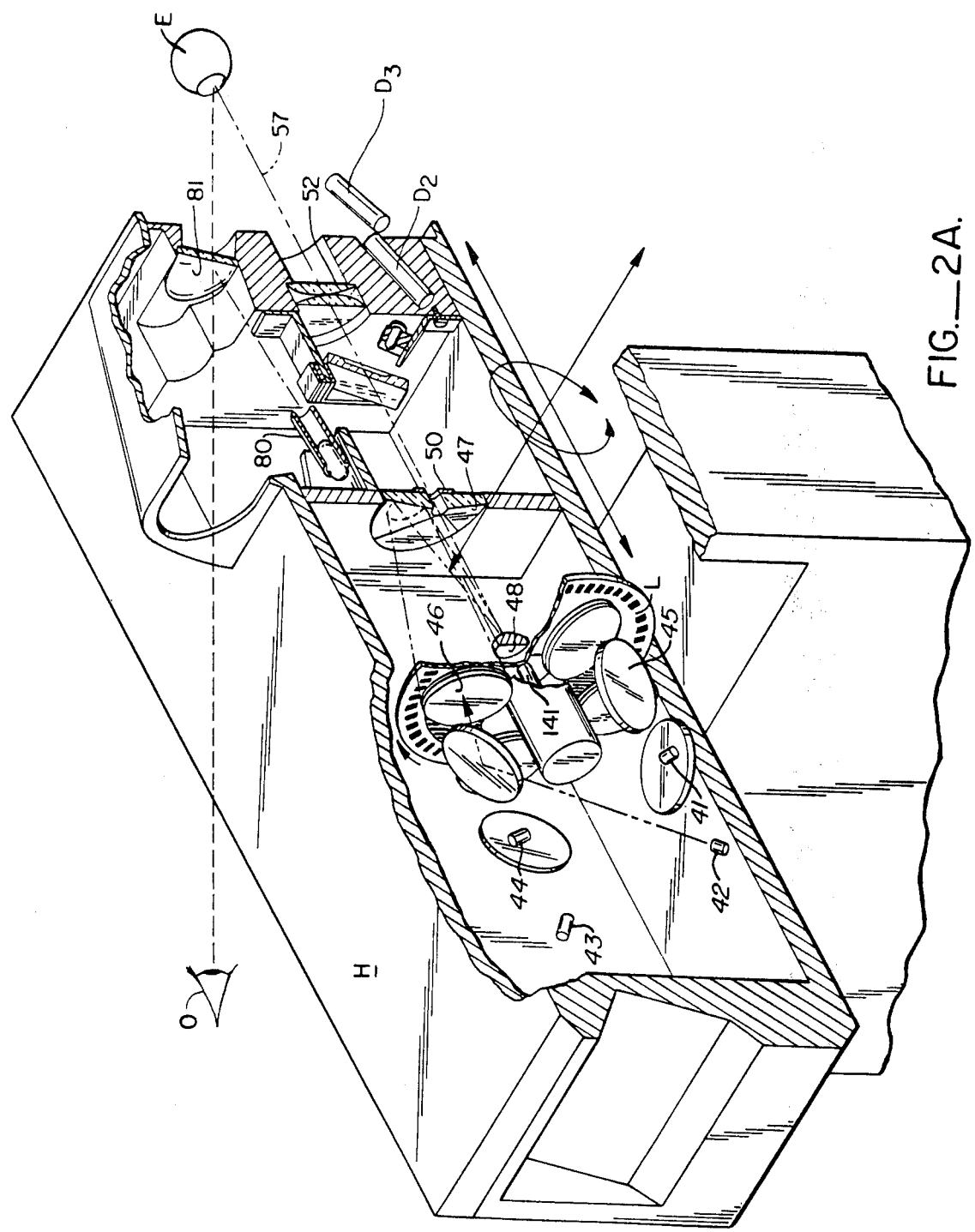
FIG._2A.

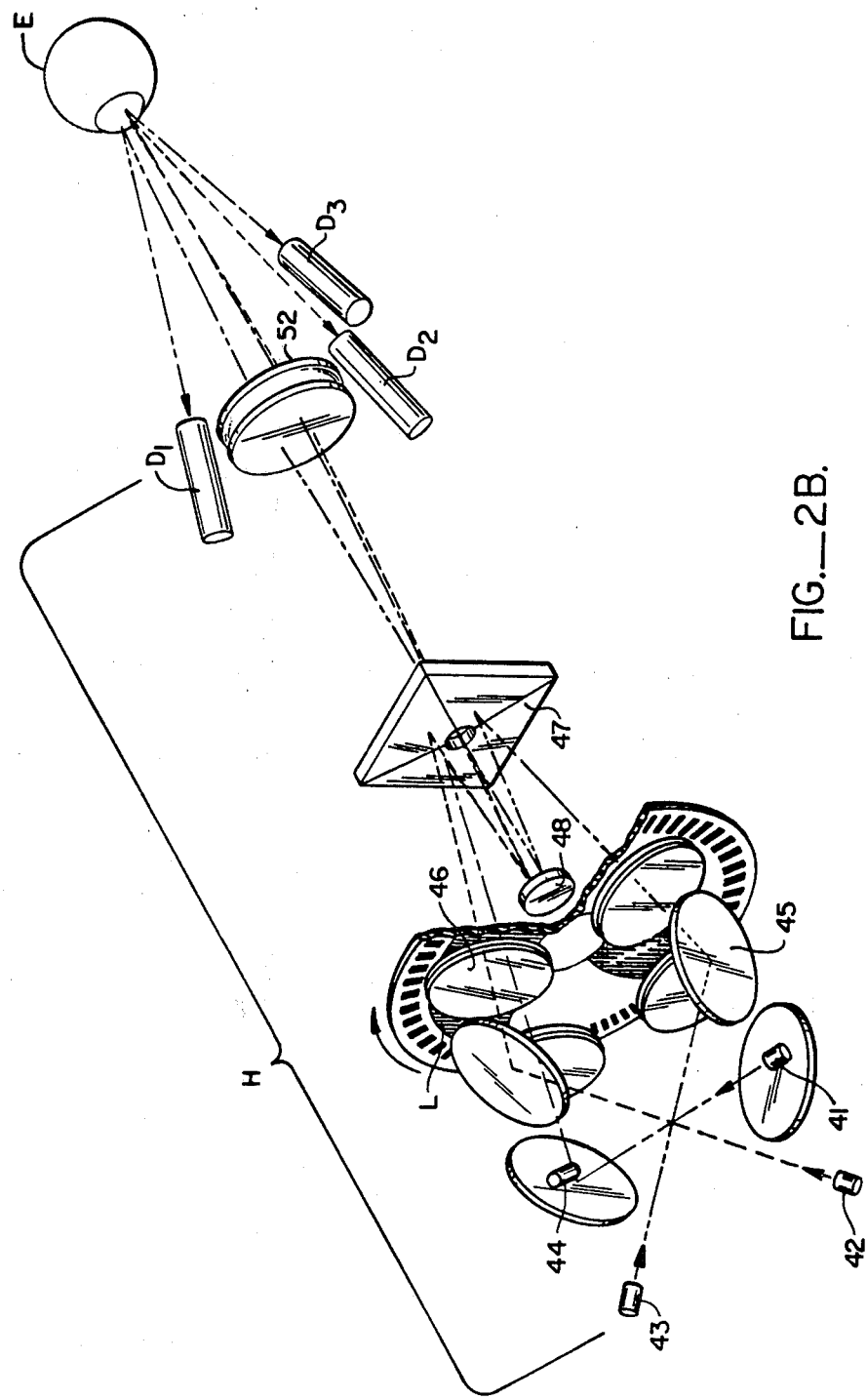
FIG._2B.

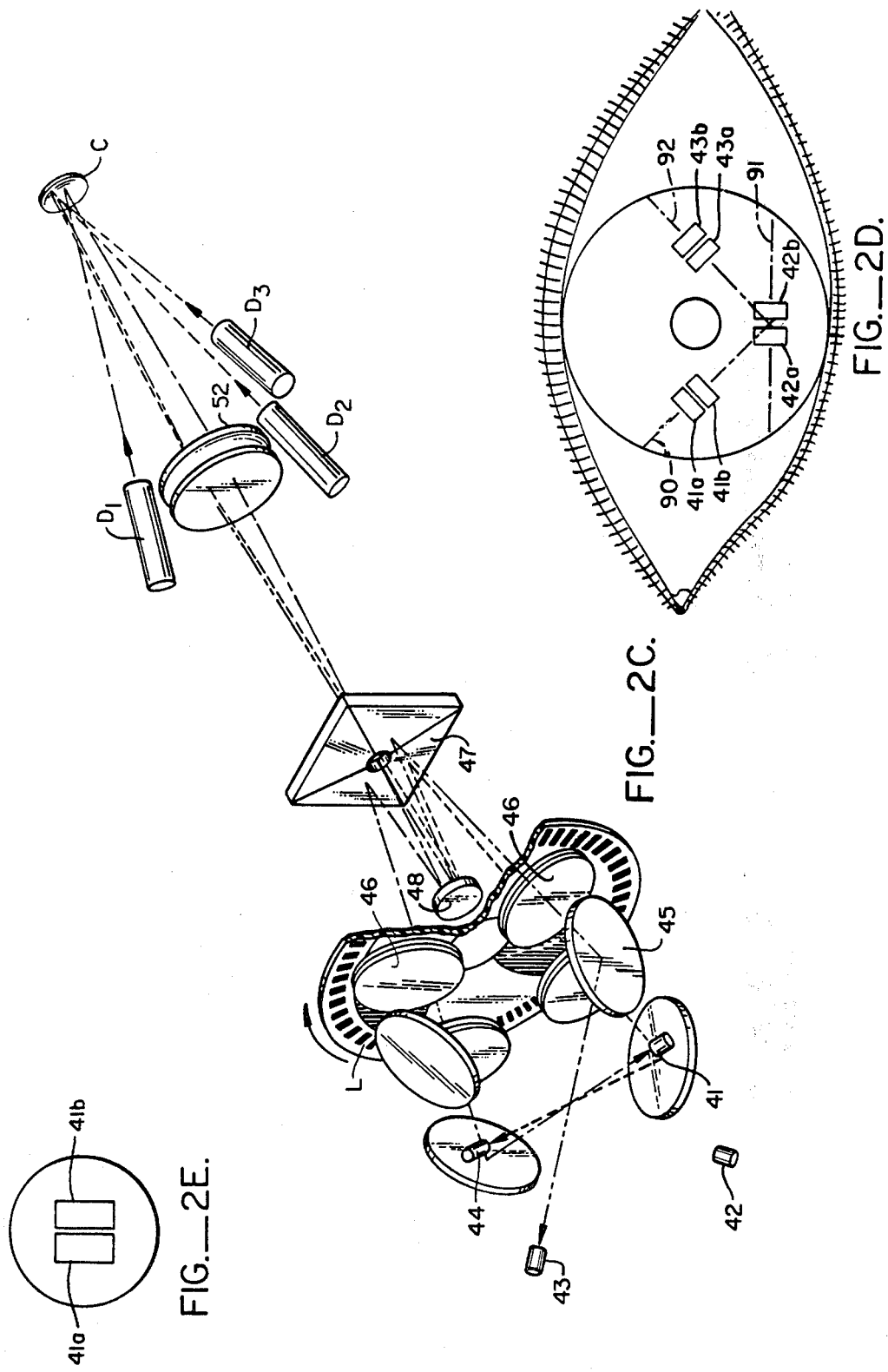

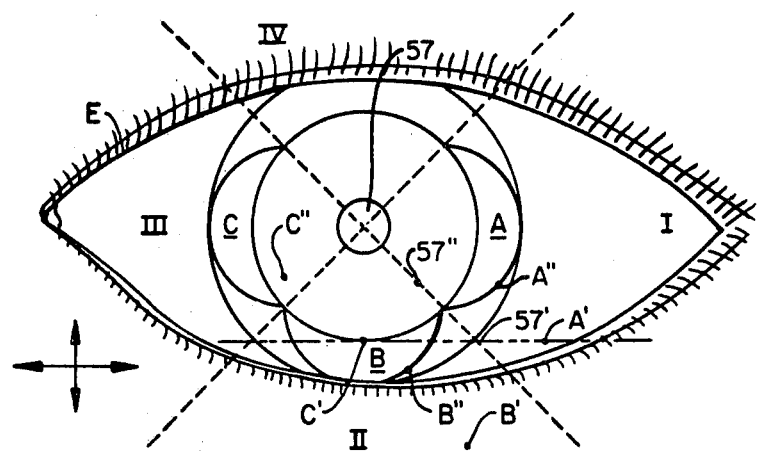
FIG._3A.
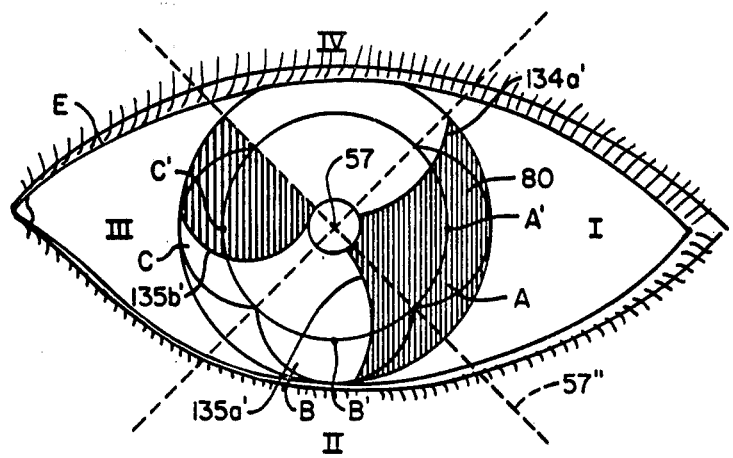
FIG._3B.
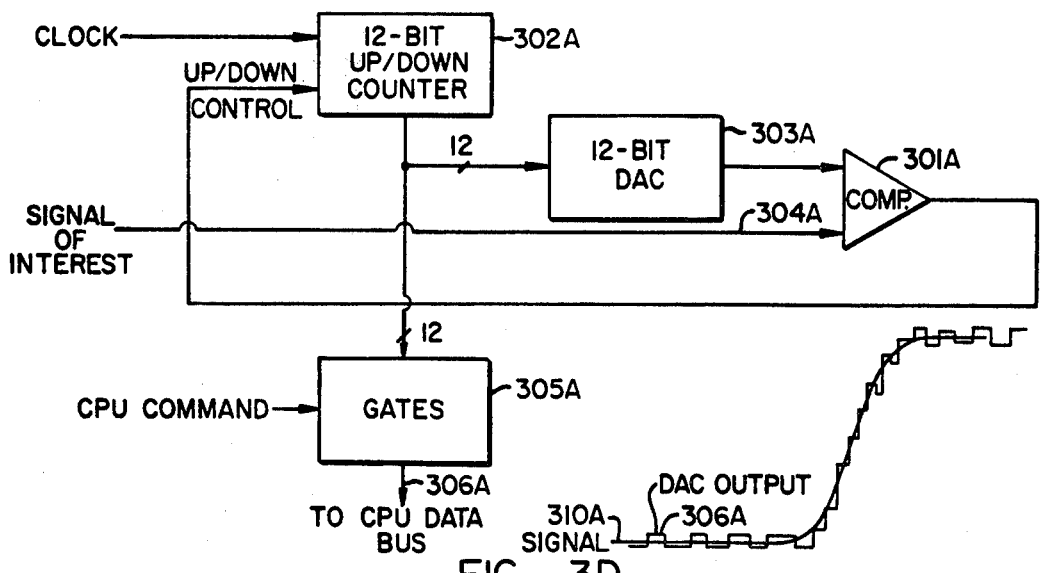
FIG._3D.

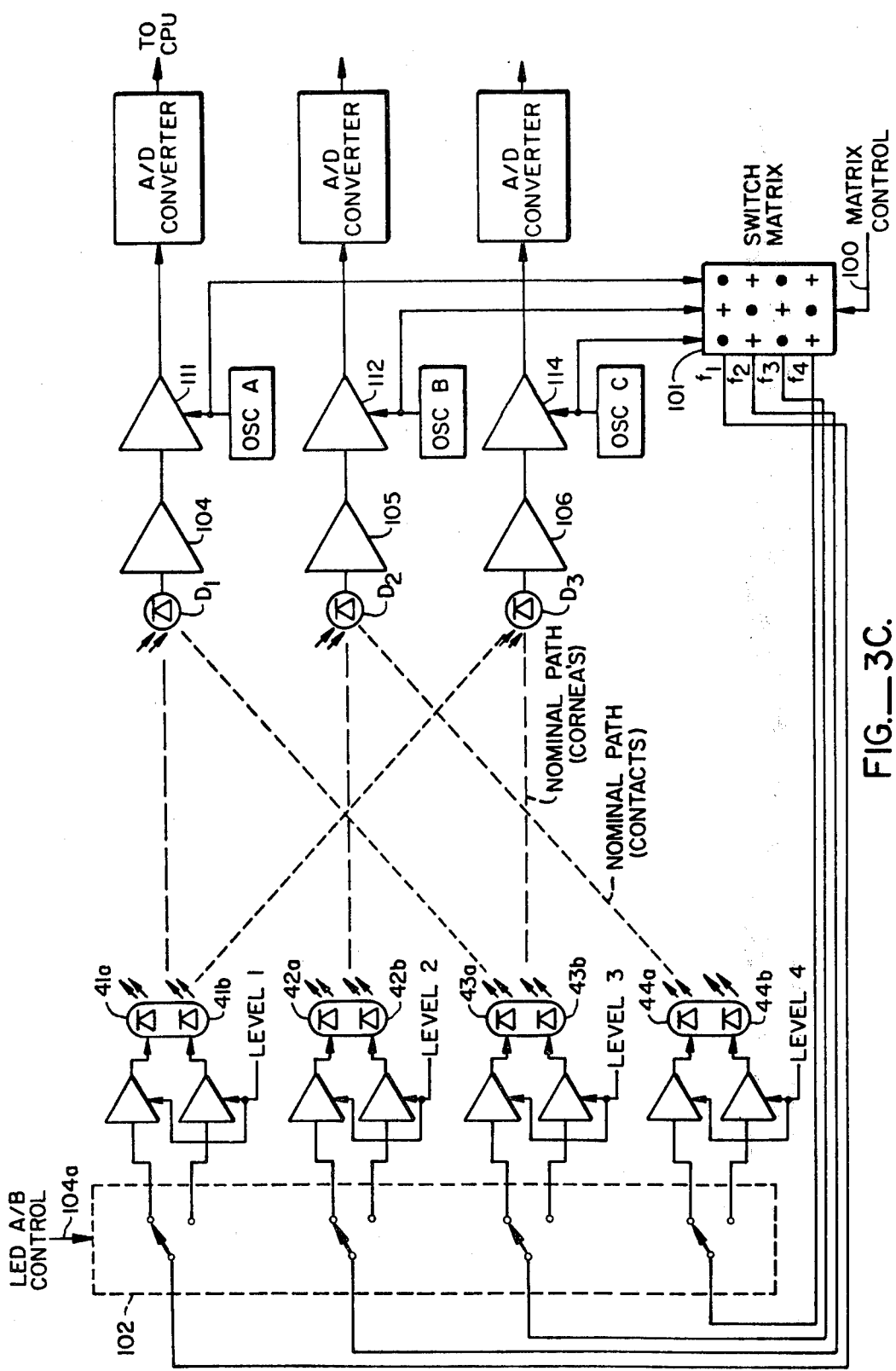
FIG._3C.

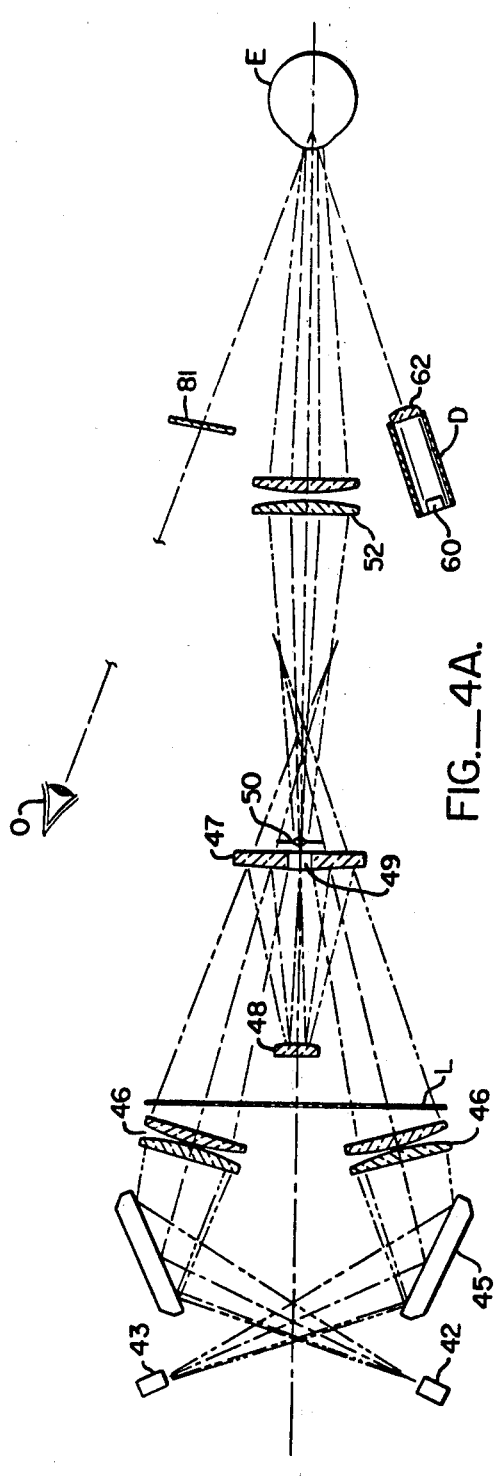
FIG._4A.
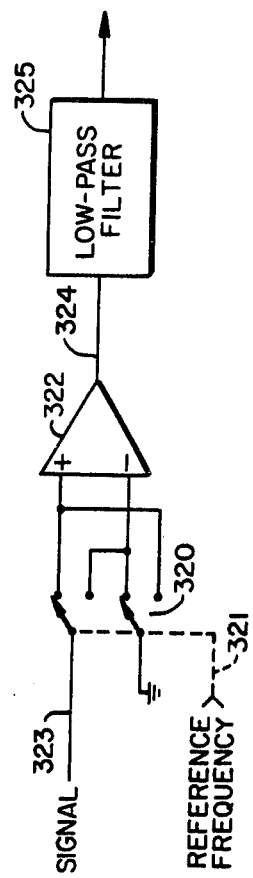
FIG._3E.

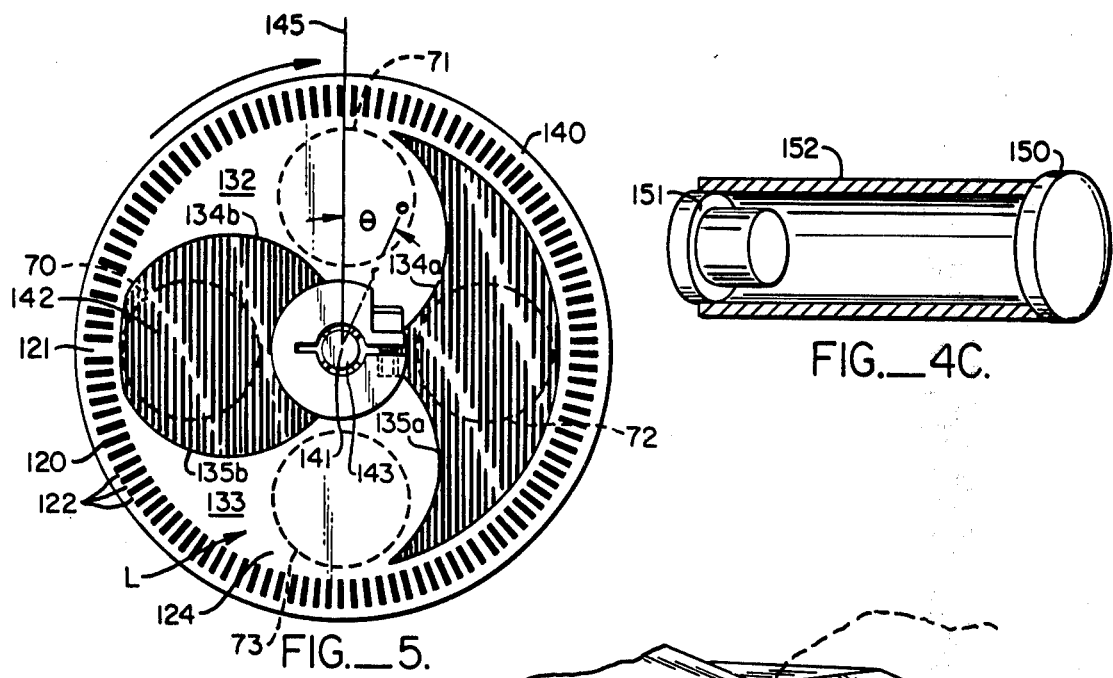
FIG._5.
FIG._4C.
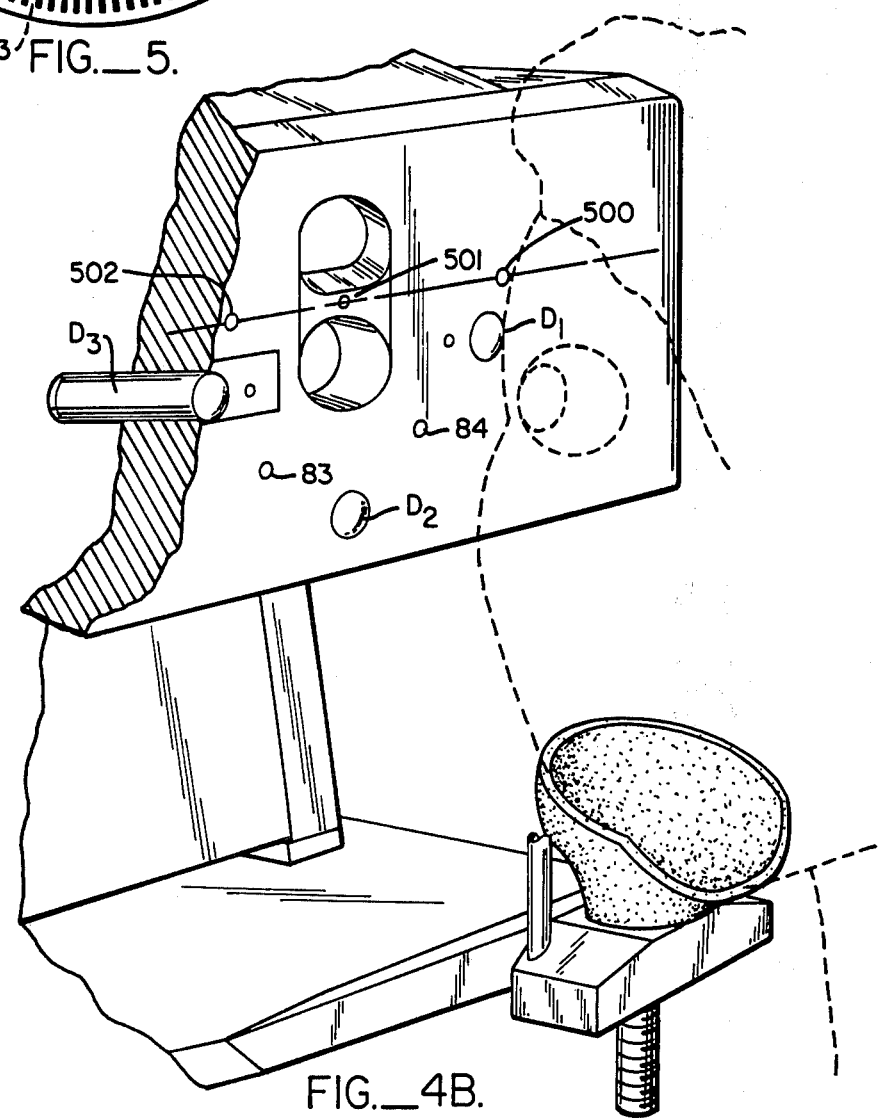
FIG._4B.

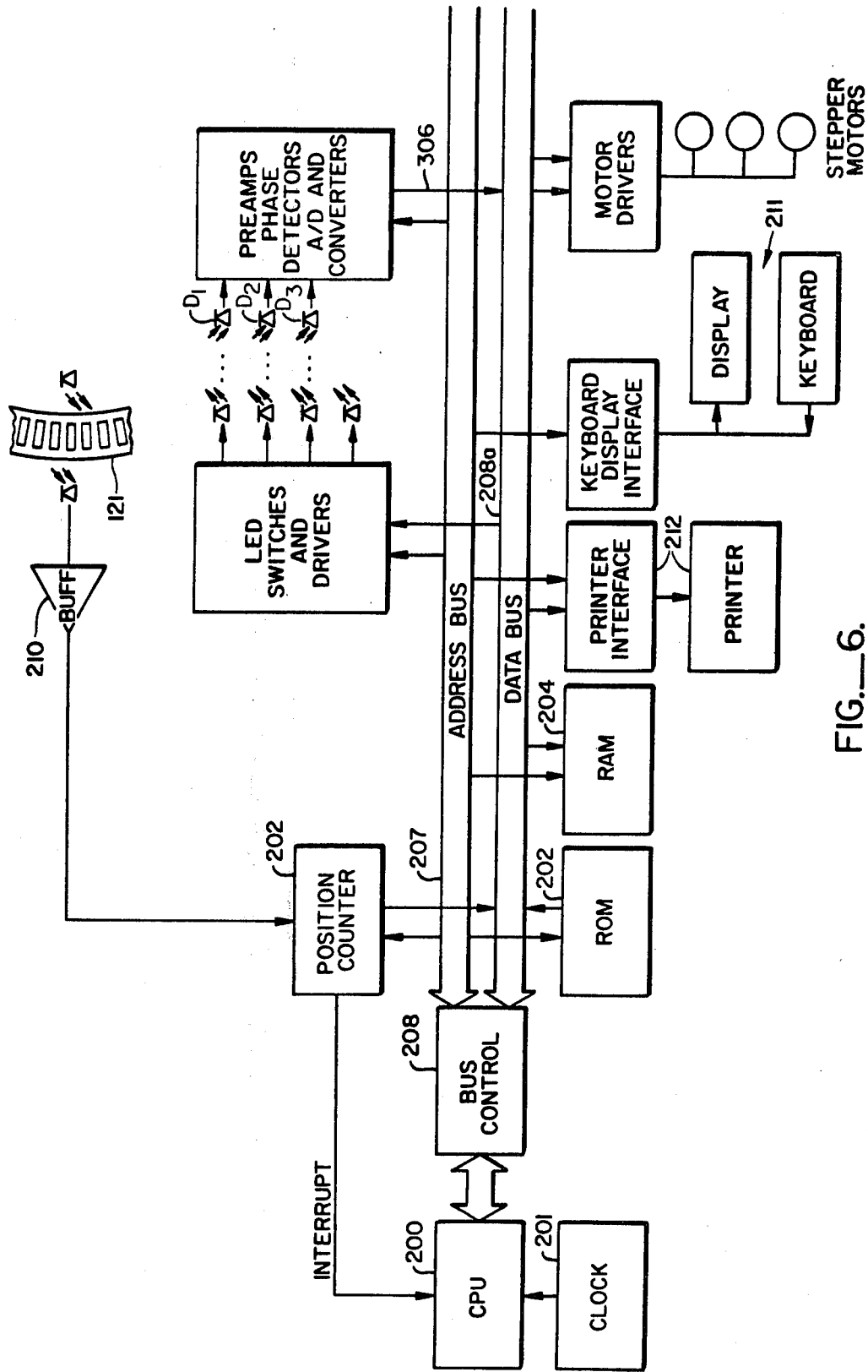
FIG._6.

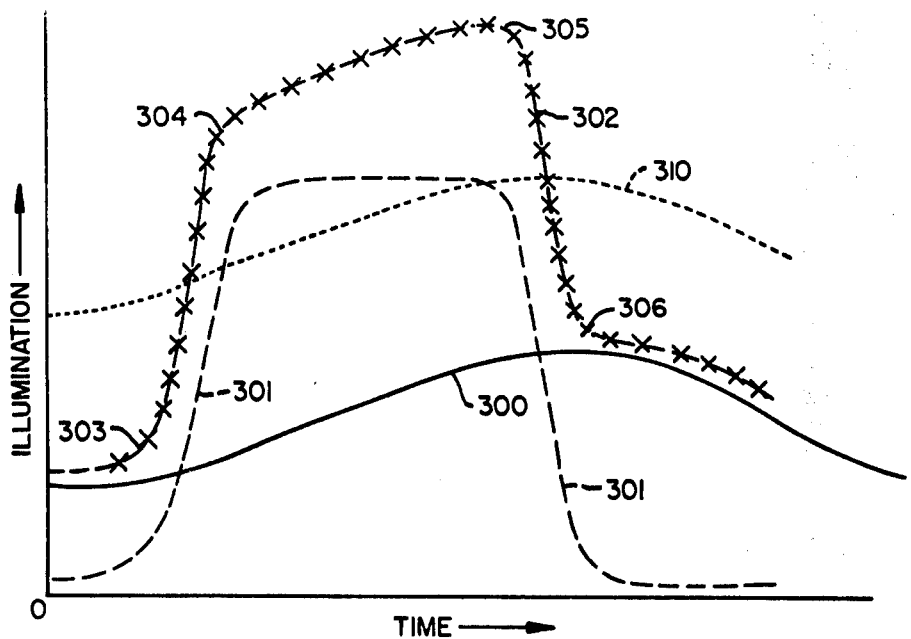
FIG._7.

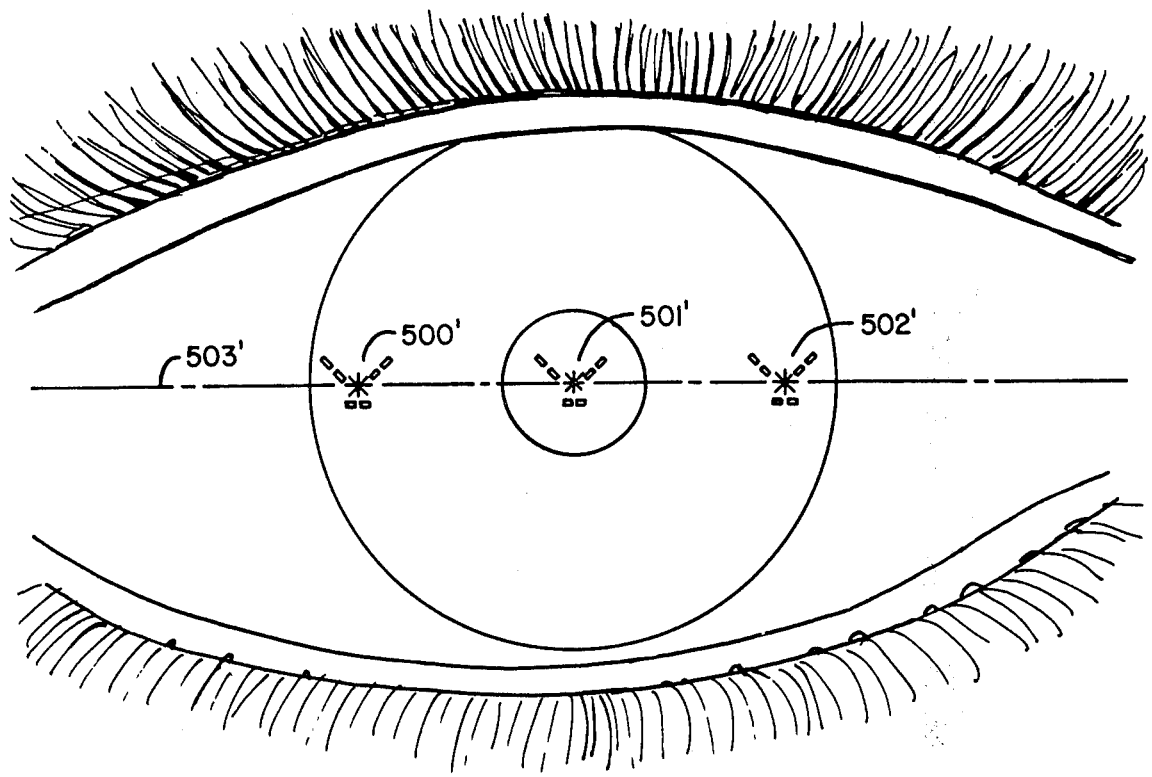
FIG._8.
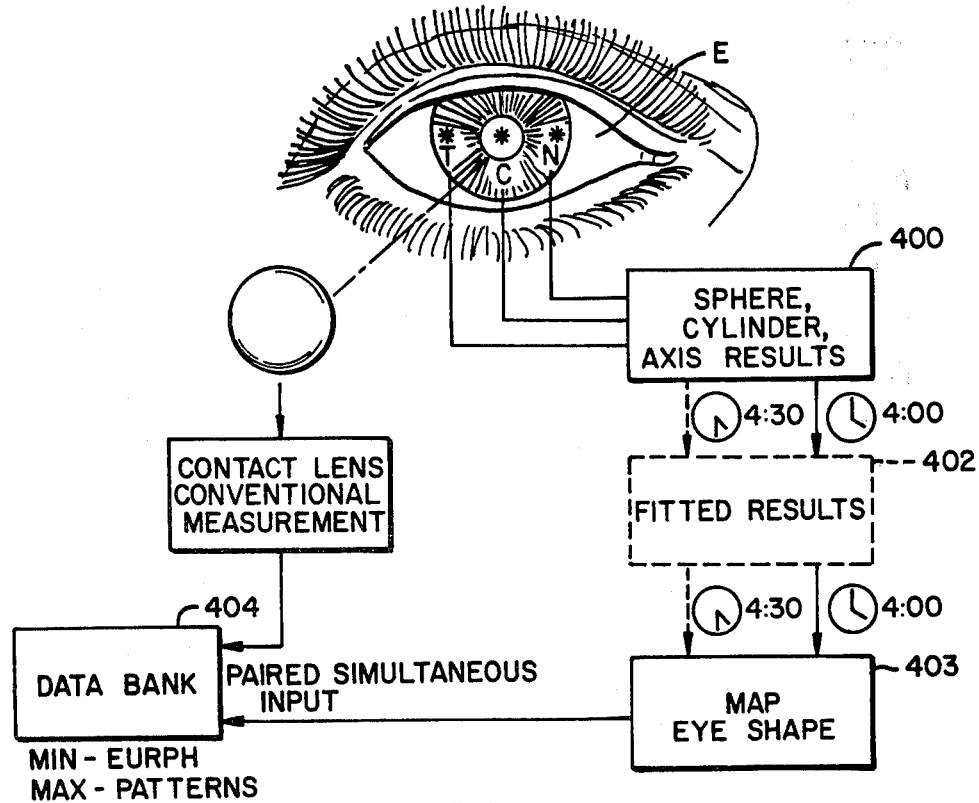
FIG._11.

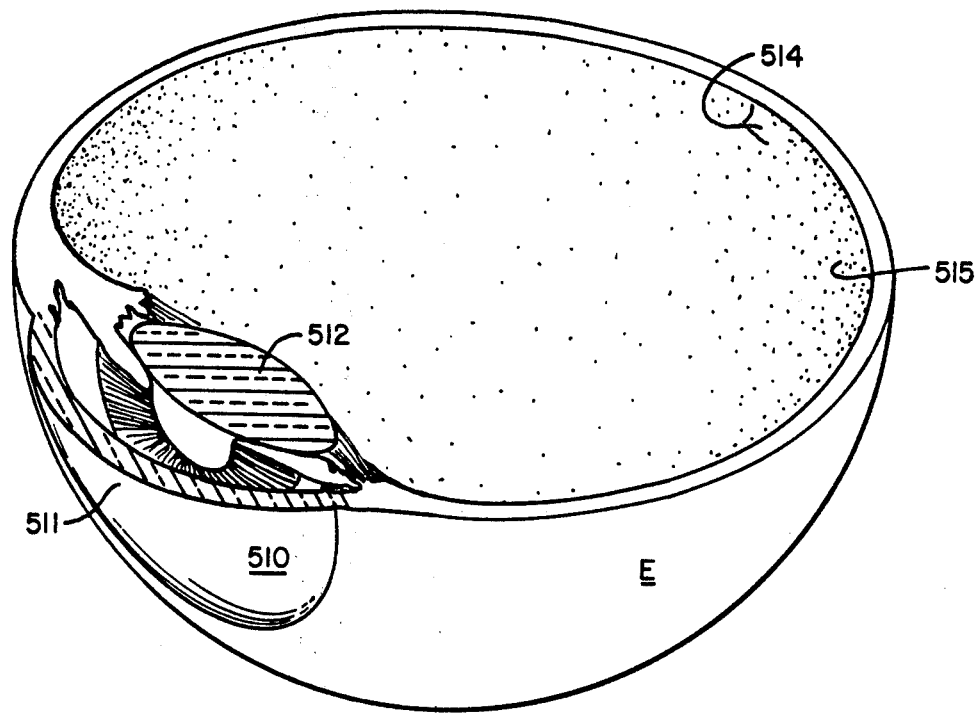
FIG._9.
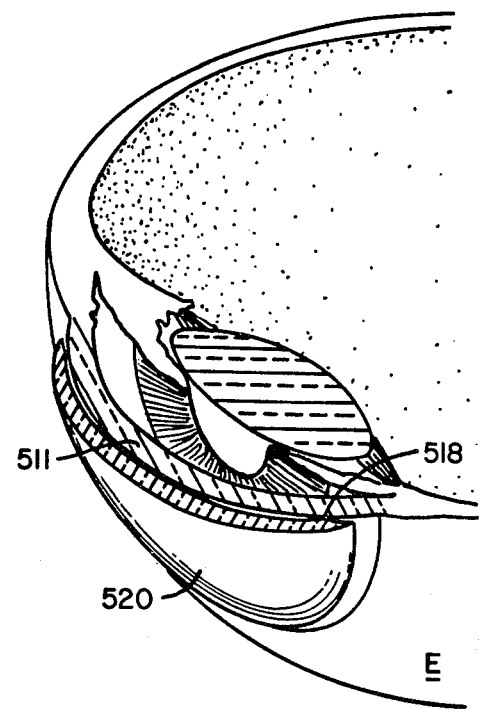
FIG._10.

METHOD AND APPARATUS FOR ANALYSIS OF CORNEAL SHAPE

This application is a continuation-in-part of recently filed co-pending patent application entitled "IMPROVED KERATOMETER," by William E. Humphrey, Ser. No. 158,849, filed June 12, 1980.

This invention relates to a method and apparatus for analyzing corneal shape. More particularly, a method and apparatus is disclosed in which the central "k" readings in equivalent sphere and astigmatism and axis are disclosed, the corneal shape parameterized, the apex of the cornea located both as to temporal up and down spacing and uncertainty of location, the cap size specified, the vault height predicted, the corrected central k computed, and a goodness of fit parameter generated which indicates the fit of the model to the particular eye being measured. Utilization of these components relative to the fitting of contact lenses is disclosed.

SUMMARY OF THE PRIOR ART

Corneal shape measurement finds its origin in early work by two brilliant ophthalmic researchers. In the year 1619, Christopher Scheiner first measured the curvature of the anterior surface of the cornea by comparing the size of the corneal reflex with the size of the reflex from a series of glass balls of different size.

The next major step forward in corneal shape determinations was made by Hermann von Helmholtz in the year 1856. Using an image-doubling technique similar to that of modern day instruments, Helmholtz devised a specific measuring instrument for the study of corneal curvatures. As a practical matter, extensive use over many years has been made of instruments similar to the Helmholtz device with the emphasis on a determination of the corneal shape at the center of the cornea—the so-called "central k reading." Those few academic studies which have ventured into the area of peripheral corneal measurements have, for the most part, also been reliant on the same optical principles of measuring the size of reflected images from the anterior surface of the cornea.

There are a few exceptions. Some studies have been carried out using a technique akin to aerial mapping. A powdery substance is scattered on the surface of the cornea and stereographic photographs of the cornea are taken. These particles on the surface of the cornea can then be brought into coincidence using aerial mapmaking techniques to produce height contours which represent the corneal shape. Naturally, such measurements have to be carried out with an anesthetized eye because of the irritation of the particle matter disposed across the cornea (soot or talc, for example). A related method employing fluorescein dye eliminates the need for anesthetic. Other studies have been carried out by taking silouette photographs of the cornea with the camera arranged 90° to the line of sight. And still further studies have been carried out by actually pouring molding material onto the cornea and then examining a positive cast of the corneal shape using calipers. These and numerous techniques including ultrasonic and mechanical tracing devices have found utility only in the laboratory. The only two currently used clinical methods are the traditional keratometer similar to that developed by Helmholtz and the more recent photographic methods referred to as photokeratometers. Each of these devices has its strengths and weaknesses. For example, the kerattometer (as it is commonly used) provides only information near the center of the cornea. Photokeratometers such as the corneascope, on the other hand, do provide peripheral information, but apparently at the expense of considerable difficulty in the analysis or a loss of precision in the measurement. (Descriptions of such photokeratometers can be found in Townsley, *Contacto*, 11(4), 1967, 72-81; Clark, *Australian Journal of Optometry*, 56(94), 1971, 94-100; Mandell and St. Helen, *British Journal of Physiological Optics*, 26(3), 1971, 183-197; and Knoll, *American Journal of Optometry and Archives of American Academy of Optometry*, 38(7), 1961, 369-397.

From this brief sketch of the history and the currently available equipment, it is apparent that the need for better information regarding corneal shape has been recognized but that no practical instrument system has yet been made available to provide the benefits of peripheral measurements at the clinical level.

The prior art has attempted to measure the curvature of the human cornea by providing fixation targets. With such targets, the eye is aligned at varying angles while the curvature of the cornea is measured. Through actual experimentation, we have found that prior art keratometers are not sufficiently accurate to generate useful information about the corneal shape. Thus, the keratometer disclosed herein makes possible for the first time the practical utilization of peripheral targets.

Several methods of parameterizing corneal shape have been suggested in the literature. These methods can be divided into two classes:

(1) those which present lists or graphs of the size of numerous departures from a reference surface for various locations on the cornea;

(2) those which attempt to distill general shape in the form of a few shape parameters.

Among schemes of the first type, deviation in corneal depth from a best fit to the central cornea (either a sphere or parabola) has been suggested (Clark, *Australian Journal of Optometry*, 57(65), 65-69, 1974; and Clark, ibid., 55(48), 1973, 48-55). This method is subject to problems in regard to the best fit procedure for a central region as well as yielding an enormous number of depth deviations that can only be comprehended in the whole in graphical form. It seems unlikely that such undistilled, detailed knowledge of the cornea can be easily used to arrive at a formalized fitting philosophy or to specify some improved class of contact lens shape, except on a unique or custom basis.

Elliptical models of corneal cross section have been shown to be effective in fitting actual populations of corneas (Townsley, *Contacto*, 14(3), 1970, 38-43). Although many authors parameterize corneal shape in terms of the eccentricity (e) of an ellipse, it can be shown that $e^2$ is far more effective and intuitive measure of corneal shape. In the "ln" model developed here, the shape parameter $\epsilon$ corresponds very much to $e^2$ in an ellipsoidal model and should be an equally acceptable parameterization of corneal shape.

Several experimental studies which have appeared in the literature on the subject of corneal shape are worth mentioning. Examples of the measurement of curvatures of individual corneas appear in Mandell's book on contact lens fitting (Mandell, *Contact Lens Practice*, 2nd Ed., C. C. Thomas, Springfield, Ill. U.S.A., 1974). These curves were developed through the use of a special small mire keratometer combined with fixation targets arranged at angular intervals from the central line of sight.

Five other investigators have published works employing the photokeratoscope technique. The first study to appear (Henry A. Knoll, 1961, supra) divided the sample of corneas into two groups—one having notable asymmetries and the other being essentially symmetrical. Combining all the results for the symmetrical corneas, a very acceptable corneal shape fit is achieved for a value of $\epsilon = 0.248$.

The second paper (Townsley, 1970) provides an interesting example of the choice of shape factor and its influence on the appearance of corneal data. This paper is a published study of 350 eyes (Townsley, 1970), but this sample includes 259 patients having a "high content of difficult cases". The published data of this paper display a format in which eccentricity (e) was chosen as the shape factor. There appear to be two populations of people peaked at eccentricities on either side of zero (spherical corneas) neglecting the question of propriety of plotting negative eccentricities.

The third paper (Robert E. Mandell and Roger St. Helen, 1971, supra) found a range of eccentricity values of 0.2 to 0.85 with an average of 0.48.

The fourth contribution (Barry A. J. Clark, 1974, supra) reveals many typical cornea properties based on an analysis of 164 keratograms. The data are fairly complete out to 2 or 3 mm and indicate a shape factor $\epsilon = 0.10 \pm 0.05$, $0.54 \pm 0.35$ diopter cylinder at 180°, 0.4 mm decentration of the corneal apex temporal of the visual axis and a cap radius of curvature of $7.759 \pm 0.260$ mm. The data show differing corneal height at the visual axis for different meridians indicating these values are by interpolation. The subjects were chosen to have refractive error less than 1.5 dopter in any meridian and less than 0.5 diopter astigmatism.

Additional information on corneal apex position is provided in the fifth paper (Tomlinson & Schwartz, *American Journal of Optometry and Physiological Optics*, 56(4), 1979, 262-240) which shows a temporal displacement of the corneal axis from the visual axis by about 0.5 mm. About 82% of the corneas had their axes 1 mm or less from the visual axis. Taking an axis 0.5 mm temporal of the visual axis would cause about 87% of the corneas to fall within 1 mm of displaced axis. The "shape factor" for the sample ranged from 0.26 to 0.60. The shape factor employed was established to be eccentricity squared. This would seem to be a sample based toward large shape factors. Corneal displacement and radial flattening were found to be inversely correlated in the temporal meridian.

Two of the papers (Mandell and St. Helen, 1971, supra; Clark, 1974, supra) provide data illustrating the extent to which individual "normal" corneas may depart from the idealized ellipsoidal model usually considered in connection with the cornea.

Taking the "parameterization" approach to describing corneal shape, it appears from the literature as a whole that the typical normal cornea can be characterized as being roughly ellipsoidal in shape with a shape factor $\epsilon = e^2/2 = 0.12 \pm 0.06$ and with the apex of the ellipsoid decentered temporal of the visual axis by 0.4 mm but with 90% of the apices falling in a 1 mm reading circle. The central "cap" of the typical normal cornea has an average radius of curvature of $7.8 \pm 0.26$ mm and $0.55 \pm 0.35$ diopters of "with-the-rule" astigmatism. Individual corneas may depart radically from the idealized "typical" cornea, both qualitatively and quantitatively.

Lens meters measure the power of the lens in at least sphere, cylinder and axis. Automated lens meters are known. For example, see my U.S. Pat. No. 4,180,325, issued Dec. 25, 1979, entitled "Lens Meter with Automated Readout" and see my U.S. Pat. No. 4,182,572, entitled "Lens Meter Utilizing Non-Parallel Light", issued Jan. 8, 1980. In both these patents, the lens meter manufactured by Humphrey Instruments, Inc. of San Leandro, Calif., now a wholly-owned subsidiary of SmithKline, Inc., of Philadelphia, Penn., is illustrated. In this apparatus, a light source appears over a broad area. A moving boundary locus is provided with a conjugate image typically focused to a detector aperture. Light from four discrete light paths is passed to a pupil or stop at the position of the lens to be sampled. The lens, in accordance with its power in sphere, cylinder and axis, causes deflection at the pupil or stop of the image of the moving boundary locus at the detector aperture. By timing successive occultations of the area light source at the detector aperture, one can determine the deflection of the boundary locus image when passing through the lens and thus determine the desired measurements in sphere, cylinder and axis.

Keratometry involves the measurement of the curvature of the cornea of the eye in at least sphere, cylinder and axis. However, applying automated lens meter technology to keratometry has proved to be suprisingly difficult. First, in a lens meter the measured lens is always positioned at the same place. In keratometry, positioning of the eye is not nearly as easy. For example, the eye cannot simply be rested upon a surface. Requiring the operator to continually position and reobserve the eye to determine that it is and that it remains in position is not acceptable for an automated keratometer. This type of positioning is used in my U.S. patent entitled "Method and Apparatus for the Corneal positioning of a Patient's Eye", U.S. Pat. No. 4,189,215, issued Feb. 19, 1980).

It is important to recognize that after the eye is properly positioned, it is a constantly moving target. Assuming that the patient maintains adequate fixation on the target, there is at a minimum the underlying saccadic movement of the eye. Complicating factors such as eye blinking and the like make the measurement of the surface of the eye a vastly more complicated problem than is suggested by any remote lens meter.

It has been found that keratometers are particularly sensitive to movement of the human eye towards and away from the instrument. A means of detecting the exact axial position of the eye with respect to a keratometer is not suggested or disclosed in the known prior art.

Standard Keratometers typically employ a target mire. In the use of a mire, a large image from known outside angles is focused onto the surface of the eye. The virtual image in the cornea of the eye is observed by the eye examiner first focusing (to obtain towards and away distance) and thereafter measuring image size on the eye. By determining along diameters a maximum mire diameter and a minimum mire dimeter, the principal axis, power of sphere and power of cylinder can all be located, measured and quantified. Difficulties determining axis at low power cylinder are present.

The difficulty of applying the aforementioned prior art to automated keratometry was in the course of my invention further complicated by a surprising factor. Specifically, in actually testing automated keratometric devices on a population of humans, I found that eyelashes of some individuals presented surprising interference with the desired measurements. These eyelash problems came from all segments of the population and were not readily identifiable prior to measurement.

It should be understood that holding or bracing of the eye lashes out of positions of interference with automated keratometric measurement is unacceptable. First, if relatively unskilled instrument operators are used, it is preferable that such operators refrain from all contact with the human eye. Second, contact with the eye can produce various accomodative movements, involuntary or otherwise, which can produce non-representative corneal deformations. Finally, holding or bracing of the lashes if improperly done can result in "temporary" corneal deformation. This unexpected problem once understood and recognized had to be surmounted.

Some means of measurement around the eyelash therefore had to be devised to allow relatively unskilled operators to make accurate keratometric measurements with the proposed instrument. It will be understood that I claim both the recognition of this problem as well as its solution to be part of my invention hereinafter set forth.

SUMMARY OF THE INVENTION

The curvature and standard dimensions of the contact lens are relatively well known. The lens in its active portion is 6.3–8.5 mm wide. Overall the lens can be 7–9.5 mm. The lens includes a base curve, a secondary curve and a peripheral curve or bevel. It is typically rounded at the edges. The typical corneal diameter is on the order of 12 mm.

The ordering and fitting of contact lenses is typically iterative. Typically, a keratometric method of sphere, cylinder and axis on the center k is taken. Keratometric reading is given, thereafter the refraction is added. Pupil size is sometimes added and the lens can be ordered.

In a more complete and diagnostic fitting procedure for contact lens fitting, the above procedure is first utilized. Thereafter, a diagnostic lens is applied. Once the diagnostic lens is applied, one observes the concentration, movement, subjective comfort, subjective vision and tear layer, possibly with the conventional fluorozene test for determining tear layer thickness. Over-refraction of the patient is then done to see what additions to prescription are made due to the present tear layer.

To date, physicians prescribe contact lenses without an accurate corneal map of the patient's eye. Lenses are commonly fitted for the first time in the presence of artificial and excessive tearing. This is due to the new and/or changed addition of the contact lens to the human eye. Naturally, without a long period of measurement, accurate measurement of the eye during the first fitting of a contact lens is not possible.

Follow-ups should be routinely done. Typically, a follow-up measurement of the patient may be done in as little a time interval as four hours. Thereafter, one week, three weeks, eight weeks, sixteen weeks checks may be used. Progress checks should be required every six months.

One of the problems that one has with contact lens fitting is the penetration of life-giving oxygen to the cornea. The cornea is typically supplied with oxygen from the tear surface over the top of it. What one wants to be careful to prevent is any kind of damage to the cornea. When a patient comes in for a follow-up, checks on central corneal clouding are performed. Additionally keratometry changes or changes in refraction, as well as corneal staining should all be observed.

The vault height for the clearance between the contact lens on one hand and the cornea on the other hand is crucial for soft lenses. In the case of some hard lenses, where large components of astigmatism originated at the "toric" cornea, by placement of a hard contact lens over the eye having a spherical surface, the tear layer filled in what would otherwise be a gap. By filling in what otherwise would be a gap, the tear layer applies a lens power.

Fitting of contact lenses thus becomes an extremely complex problem. Calling the role of the refractive surfaces, we have the eye and tear layer. Thereafter we have the tear layer and the contact lens. Finally, we have the contact lens and the atmosphere.

When we fit a patient with contact lenses, the three basic things we are after are:

a. Comfort;
b. Vision improvement;
c. Corneal physiology unchanged.

All these factors can be vastly improved by using the method and apparatus of corneal modeling that follows.

An analysis of the corneal shape through the combination of several keratometer measurements is disclosed. The eye is preferably scanned to a nasal angular position, a central angular position and a temporal angular position. The central position is straight ahead along the patient's line of sight. The temporal and nasal positions are in the broad range of up to 5° to 22°; the intermediate range of 10 to 15°; and the narrow range of 12° to 14° on either side. Measurements in sphere, cylinder and axes are taken. Astigmatism is in the more preferable format of 0°–90° astigmatism and 45°–135° astigmatism. When each individual point is measured with its respective estimage for sphere and cylinder components, these measurements are fitted to an idealized parameter. Then the three sets of curvature measurements taken at the specified locations are reduced to a set of adjusted, idealized curvatures all fitted to an elliptical model. Thereafter, these fitted values create final corneal shape parameters, the particular process here including the creation of intermediate parameters. Finally, readings of central "k", corneal shape, apex position, cap size, vault height, corrected central "k" and goodness of fit are all set forth.

A keratometer is disclosed for remotely measuring corneal curvature in at least sphere, cylinder and axis. Assuming the eye is precisely positioned for measurement, light sources are overlapped and imaged to a virtual image position behind the human cornea. These sources of light—preferably three in number (although more than three can be used)—each have their own discrete path from the source to the eye and thence to their own discrete detector. Between the light source and the eye, the light traveling along each light path is interrupted by a moving boundary locus having a transparent portion, an opaque portion and a boundary therebetween. The moving boundary locus is in turn imaged by reflection from the cornea being measured to a real image position superimposed to and upon a light detector. The detector for each eyepath is aligned to and towards the virtual image produced by the light source in the precisely positioned eye. Stray light emanating from positions other than the vicinity of a virtual image position of the light source in the cornea cannot be received by the detector. By measuring the displacement on the eye of the virtual images of each moving boundary of the locus with its associated discrete light path, a keratometric measurement can be made with as few as three light sources, three detectors and three separate and discrete paths therebetween. A preferred geometry of the eye interrogation pattern is disclosed in which two horizontally spaced points and a third medial and lower point are simultaneously interrogated. Omission from use of the upper portion of the pattern avoids interference which can be caused by the upper eyelash. These points are angularly spaced by 90° intervals from the optical axis of the instrument, thereby permitting similar measurement of the concave surface of contact lenses with the preferable addition of a single extra light source (or detector). For automated eye acquisition, each light source—preferably in the infrared—is provided with two discrete diodes, which diodes, when the eye is optimally positioned in distance towards and away from the instrument along the optical axis, are simultaneously occulted by the moving boundary locus. Where the eye is axially out of position telltale shifting of the optical center of the dual light sources alone or in combination with accompanying shifting of other dual light sources signals axial misalignment. Improper axial eye position can be detected by shift of the dual light source optical center alone. Preferably the produced shift can be analyzed by a microprocessor for both position and presence of non-toric surfaces (the latter being an indication of corneal irregularity). This analysis is not interrupted by natural eye movement, such as saccadic eye movement. An embodiment of the moving boundary locus which has opaque transmissive boundaries sweeping each of the light paths substantially simultaneously minimizes the ever-present movement of the human eye by producing an effective high shutter speed for measurement. The dual light sources are given a coded oscillation, to be detected and identified, the identity used to move the instrument transversely of the eye from a gross instrument alignment to and towards the precision alignment required for corneal measurement. A wholly automated apparatus and process for keratometry results.

OTHER OBJECTS, FEATURES AND ADVANTAGES

An object of this invention is to provide a keratometer with an automatic eye acquisition feature. According to this aspect of the invention, at least three light sources are imaged to three discrete areas of the human eye. Each of the light sources is coded by intensity modulation. Each of the detector areas is capable of looking at and detecting which light source is incident upon that particular area. Once the instrument is grossly aligned so that any of the three light sources hit any of the three detector areas, the light source is recognized and the instrument translates to effect full acquisition.

An advantage of this aspect of the invention is that the instrument can first be grossly aligned using the operator viewing along a direct line of sight and registering a virtual image to the eye being observed. Thereafter, automated eye acquisition as above described can be used with minimum amount of instrument movement to precisely align on the eye.

A further object of this invention is to disclose a system of detecting towards and away eye movement for proper distance calibration of the eye axially towards and away from the instrument. According to this aspect of the invention, each light path includes an area for light emission which includes two sources of light, these sources typically having a discrete area of light emission. Each of the paired light sources for each optical path is in effect oscillated or timed in its emission, such that the detector for that path may recognize the particular light source emitting photons. When the instrument is properly positioned, occultation by the boundary of the moving boundary locus causes both light sources in each light path to have an essentially constant optical center of occultation. Where the light sources are out of position, the paired light sources undergo movement with respect to the time of occultation of their detected optical center. This movement gives a telltale indication which can be remotely monitored that the monitored eye is out of position and that the instrument requires movement in distance positioning together with the required direction and amount of movement necessary to result in optimal positioning.

An advantage of the paired light sources is that a single optical path having two light sources can be sufficient for distance calibration. Assuming the eye to be an essentially stationary object, merely telltale movement of the detected optical center of the light sources will be sufficient to indicate errors in distance positioning.

Yet another object is to disclose the utility of employing paired light sources for each of three optical paths. According to this aspect of the invention, each optical path is provided with paired light sources. Two of the light sources are typically aligned along axes at 90° one to another. A medial light source is aligned substantially obliquely to the axes of both light paths and typically displaced from an axis extending centrally between the two light sources. The optical center shift for a first group of light sources—one from each light path—is measured. Thereafter, the optical shift of another group of light sources—the remaining source from each path—is measured. These measurements are then used to determine towards and away distance position.

A further object of this invention is to use the immediately above-described paired light sources for each optical path to examine for possible non-toric surfaces. Where non-toric surfaces are encountered, a measurement can be rejected and the eye examiner warned by the rejection that patient with a possible non-toric cornea is being examined.

In the foregoing, it will be appreciated that only three light sources are used. Those having skill in the art will appreciate that more than three can be used. For example, a system of four detectors can be utilized.

An advantage of the above-described aspect of this invention is that the problem is positioning the patient towards and away from the keratometer by focus is avoided. Moreover, optically compensated paths are no longer required. Instead the disclosed keratometer can be remotely positioned towards and away from the eye to a precisely determined distance. Intimate operator attention to keratometer positioning to obtain the measurement and during the duration of the instrument measurement is no longer required.

A further advantage of the automated eye positioning mechanism is that the resultant measurement is more accurate; errors due to unfavorable instrument positioning are not present.

A further object of this invention is to disclose a pattern for point source keratometric measurement of the eye. According to this aspect of the invention, three points on the cornea are measured about an optical axis. Two points are substantially horizontally aligned and on opposite sides of the optical axis. The third point is below a line through the optical axis and on the corneal surface of the eye. Preferably all three measurement points are separated by 90° intervals. That 90° interval which is vertically above the optic axis is omitted and not used.

It has been found that the above eye measurement pattern, that of not having a point at the upper portions of the eye, avoids a surprisingly difficult problem of interference of human eyelashes with keratometric measurement. That substantial random portion of the population which have inherently interfering eyelids can be measured utilizing the above pattern because the upper eyelash will not interfere with the light impinging upon the eye.

An advantage of the avoidance of interference of human eyelashes with the disclosed keratometric measurement is that the eyelashes do not have to be manipulated. Having an eye examiner reach close to the delicate surface of the eye is avoided. Touching of sensitive areas of the eye, such as the sclera, is avoided.

A further advantage of avoiding manipulation of the eye is that physical and autonomic deformations of the cornea are avoided or at least minimized. It is known that the cornea deforms for finite lengths of time.

A further object of this invention is to disclose the utility of the three point source of measurement used. According to this aspect of the invention, the analyses of the three points to determine the desired keratometric measurement is disclosed.

A further object of this invention is to use the same light impingent pattern on the eye as for the complementary measurement of the equal and opposite surface which constitutes the inside portion of contact lenses. According to this aspect, the same light pattern is generated for measuring contact lenses. A second vertical source is added to project the light source in a new position. By the simple addition of a single source, complementary curving surfaces of contact lenses can be measured.

An advantage of this aspect of the invention is that the same instrument can be used for the remote measuring of contact lenses as well as the remote measuring of the human eye. Consistency of matching contacts to the eye by using the same measurement standard is possible.

A further advantage of this invention is that the light sources and detectors are essentially interchangeable. While such interchange may provide varying trade-off with respect to the disclosed optical design, it will be understood that reversing of the light paths is feasible.

A further advantage is that the light sources can be point sources of high intensity infrared light. These sources are chosen to be below the threshold that could possibly have physiological effect on the eye but small enough in area so that eyelash interference is minimized. The advantage of point sources of light becomes even more pronounced where viewing through the eyelashes is required.

A further object of this invention is to disclose a light path. According to this aspect of the invention, dual light source detectors are located behind the moving boundary locus. Single infrared emitters emit light onto the cornea.

An advantage of this aspect of the invention is that the light sources can essentially be point light sources. The use of high intensity point light sources minimizes any interference which eyelashes may cause to the disclosed keratometric measurement.

A further object of this invention using three point sources herein disclosed is that screening for nontoric functions can result. Consequently, measurements which exceed a given threshold can be rejected. With such rejection, cases of instrument measurement with highly erroneous readings are avoided. Moreover, abberations of the eye from the norm can be detected. For example, cases of kerataconus, along with other corneal deformations, can be looked for upon instrument rejection of a candidate for keratometric measurement.

A further object of this invention is to disclose a system of automated measurement of spaced points of the eye on substantially a simultaneous basis. According to this aspect of the invention, the three chosen point sources of light are imaged to the eye. A moving boundary locus is chosen having at least three similarly spaced boundaries. The boundaries are such that the eye is swept at all three points at substantially the same time interval by the locus. There results simultaneity of image sweep at the eye points.

An advantage of this aspect of the invention is that greater accuracy can be achieved even though the eye is moving constantly during the measurement. By applying a very high "shutter speed," the resultant movement of the eye can be neutralized. Thus, the natural movement of the eye is in effect neutralized by the disclosed instrumentation.

An object of this invention is to disclose a process and apparatus for mapping the contour of the human eye. According to this aspect of the invention, a keratometer is provided with central, temporal and nasal fixation points. The central fixation point corresponds to a straight ahead eye view. The nasal and temporal points depart from the central view by angles in the range of between 5° and 22°, in the intermediate range of 15°–10° and in the narrow range of 12°–14°. Discrete measurements of sphere, cylinder and axes are taken at each fixation. These fixation measurements are thereafter idealized to fit an elliptical mode. From the elliptical model, at least one of the following measurements is generated:

Central "k" readings in equivalent sphere, axis and cylinder;

A corneal shape factor;

An apex position, including horizontal and vertical displacement as well as an uncertainty factor in locating the apex;

Cap size;

Vault height (in millimeters over a 25 mm diameter sclera); and

Corrected central "k" and a "goodness of fit" factor indicating the performance of the model to the measured eye.

An advantage of the disclosure of this invention is that for the first time commercialization of fixation points in measuring the human cornea can be made. The accuracy of the disclosed keratomer now permits corneal modeling in the disclosed elliptical format.

A further advantage of the disclosed method of mapping is that the provided shape parameters do include some intuitive inputs that may be utilized by the practitioner to visualize the surface being mapped.

A further object of this invention is to disclose a process apparatus for fitting contact lenses. According to this aspect of the invention, measurements of the contact lens and the provided corneal map are taken for fitted contact lenses having high degrees of comfort. A data bank of stored information is created, which data bank includes at least one or more of the following parameters from a measured human eye:
Central "k";
Corneal shape;
Apex position;
Cap size;
Vault height;
Corrected central "k"; and/or goodness of fit.

Measurement of the contact lens is conventionally made and the data likewise stored with the data of the map corresponded to the data of the fitted lens. Maps of eyes measured are compared against the stored data in the table. There can result vastly improved fitting of contact lenses.

As of this writing, the claimed apparatus and method capable of making the measurement are now created and are fully disclosed herein. Although data indicating a correlation between the map of the eye and the dimension of contact lenses needed to fit individual eyes from the total population of eyes capable of being mapped have not yet been accumulated, such data are in the process of being generated and can be generated using standard statistical techniques.

The reader should be aware that I claim utility in the measurements generated. Specifically, the claimed utility can be derived into two broad classes of benefits.

The benefits of additional corneal information can probably be divided into two types. The first benefit is associated with the fitting of contact lenses. Additional corneal information can be used in the fitting of contact lenses in several ways. For example, at the preliminary fitting stage, an analysis of corneal shape can result in the judgment of the optical suitability of contact lenses to individual patients. The shape of the cornea can have many implications in the analysis of a patient's potential for good vision. The degree of departure of the cornea from a sphere, as well as misalignment of the cornea's axis of symmetry, are all potential sources of optical aberrations—including astigmatism and even more complex forms of aberration. One has often heard the story of patients whose vision is degraded somewhat through the use of contact lenses. However, the converse may occasionally also be true, i.e., contact lenses may actually increase the visual acuity of some patients. The source of these optical trade-offs has been analyzed in the literature (Ludlam and Wittenberg, *British Journal of Physiological Optics*, 23(3), 1966, 178-184). It is a simple extrapolation of these results to say that by knowing the departure of the cornea from a spherical shape, it might also be possible to choose the lens type most likely to result in high visual acuity, for example, by minimizing the effects of spherical aberration (Campbell, *American Journal of Optometry and Physiological Optics*, 58(3), 1981, 212-217). Corneal shape information may also lead to better estimates as to the dynamic performance of a contact lens as it will perform in place on the patient's eye. For example, estimates of contact lens motion during blink or the choice regarding hard contact lenses vs soft contact lenses may all be somewhat dependent upon knowledge of the corneal shape.

Going on to the second phase of contact lens fitting, after the suitability of contact lenses has been determined or the selection of type has taken place, corneal shape information can be expected to be a benefit in the actual contact lens fitting procedure. Traditionally, a "central k value" is taken to pick a trial contact lens, and, at least in the case of hard contact lenses, there is a strong reliance on the use of fluorescein patterns to modify the choice of trial lenses in order to take into account by peripheral effects of the corneal shape. A better first try should be possible with a greater knowledge of the corneal shape in the peripheral as well as the central regions. The benefit to the patient is the perception of increased professionalism and reduced discomfort from repeated trials; the benefit to the doctor is a more comfortable patient and a reduced examination time.

Now, going on to the second general use of corneal shape information, there is the matter of monitoring changes of corneal shape over intervals of time. Generally speaking there are two common situations in which this is of interest. One of them is in the case of a pathology, for example, developing keratoconus. Routine examinations can help the doctor establish the state of progress of the disease and determine the effectiveness of treatment. Another common reason to monitor corneal changes over time has again to do with contact fitting. It is generally accepted that a patient's routine use of contact lenses should not have the effect of producing substantial changes in corneal shape. Periodic central as well as peripheral measurements of the corneal shape during the first months of patient use can help the doctor satisfy himself that the contact lenses are indeed having minimal effect upon corneal shape.

Now we will consider some detailed mathematical models for the corneal shape. This is accomplished by scaling all dimensions in terms of the radius of curvature at the apex of the cornea. By taking the sagittal depth of the cornea in units of the central radius of curvature and representing that as a function of the radial distance from the corneal axis of symmetry, again in terms of units of central radius of curvature, it is possible to characterize entire families of corneas having entirely different scales of size but having similar shape through the use of a single shape parameter. In this way, dimensionless analysis of the corneal shape simplifies the manifold of possible corneal shapes that has to be dealt with as an entire family of shapes can be derived from a single set of tables or a single set of relationships simply by multiplying appropriate variables by a scaling factor, which is the central radius of curvature.

There is a second advantage to the dimensionless analysis. A dimensionless representation of the cornea ignores the linear scale of size but preserves the angular scale of cornea shapes. When fixation sources at specified angular intervals from the central fixation are employed, the corneal sampling areas occur at fixed values of the dimensionless radius for any given shape factor. This contributes to simplifying the mathematical analysis.

In the analysis which follows, the symbol $\zeta$ will represent the sagittal corneal depth in dimensionless form and $\eta$ will represent the corneal radial distance in dimensionless form; these two terms will be related by functional relationships involving only one other parameter, specifically the corneal shape factor which is also dimensionless.

A shape model for the cornea has been developed based on a combination of known anatomical features of the corneal structure as well as upon various assumptions having to do with the physics of the fluid statics and of the distribution of stresses at the corneal surface. It is assumed that the corneal shape is maintained by layers of strap-like tissue members called lamellae. It is further assumed that the lamellae of the eye are distributed in such a way that they all sustain approximately the same tension per fiber. The lamellae are assumed to pass as uninterrupted bands entirely across the cornea. There is an observed thickening of the cornea toward the periphery amounting to something like a 20% thickening at 6 mm from the center of the cornea. (This result is reported by mandell and Polse, *American Journal of Optometry and Archives of American Academy of Optometry*, 46, 1969, 479 although there are differing results reported elsewhere, such as Smith, 1977). The assumption is made that this thickening is a result of additional density of lamellae. (One interesting, semi-quantitative result of these assumptions dictated by fluid statics as well as the equality of the radial and tangential fiber tension leads to the conclusion that toward the periphery of the cornea the growth in the density of radial fibers will be only ⅓ as great as the growth of tangential fibers because the hoop tensions must grow more rapidly than the radial tensions. Hence, this accounts for a larger portion of the corneal thickening toward the edge of the cornea.)

Based on this meager input of assumptions and data, it is possible to develop a mathematical model capable of predicting several known properties of the cornea. Aside from having the correct corneal thickening, which is input information, the model would predict approximately 3 diopters curvature reduction at 3 mm from the center of the typical cornea which is in reasonable agreement with measured variations. (The model predicts somewhat greater departures from a spherical corneal than most studies in the literature.) The model would also predict a sagittal height for a cornea of average diameter of 2.58 mm while the measured value is 2.59±0.22, again in excellent agreement; and the slope of the cornea at its periphery is nearly tangent to the opening in a 25 mm sphere representing the scleral shell, again in good agreement with observations and consistent with the hydrostatic requirements for this model of the eye. It is a very encouraging result to have a corneal model with only one free parameter which is reasonably consistent with so many known physical measurements of the cornea.

However, a word of caution is in order. Although the corneal model may be in excellent agreement with the average values for a large ensemble of corneal measurements, the very process of averaging measurements tends to have a smoothing effect on the possible variations that any particular individual cornea may have. The success of this mathematical model of the cornea, then, depends upon the shape parameter and corneal apex location being the dominant effect in describing the shape of the cornea over and above the individual corneal variations.

There is almost certainly going to be some small fraction of the subjects for whom this condition does not hold. Perhaps the first important point to bring out is that I have discovered what might be termed a three-to-one rule. This rule states that for any reasonably smooth corneal shape model, the variation of the curvature of the cornea measured from the axis of symmetry will show three times as large a variation for the curvature in the meridional (radial) cross section as it does in the sagittal (tangential) cross section. Since the difference in the curvatures in these two cross sections can be interpreted as a component of corneal astigmatism, it becomes apparent that changes of corneal astigmatism are a direct measure of the corneal shape factor as are the more commonly used variations of curvature along the radial cross section. This valuable information in regard to corneal shape which resides in the change in corneal astigmatism has been neglected possibly as a result of ignorance of its importance and possibly because of the difficulty in the mathematical analysis of changes in the astigmatish. It will be immediately apparent that both the 1n model and the ellipsoidal approximation obey the three-to-one rule.

In the following description and especially in the claims, it will be understood that I refer generically to eyes and contact lenses as optical surfaces with curvature or words of the like effect.

Other objects, features and advantages of this invention will become more apparent after referring to the following specification and attached drawings in which:

FIG. 1A is a perspective view of the instrument illustrating the various degrees of motion of the instrument about the patient for automated acquisition;

FIG. 1B is a partial section of FIG. 1A illustrating the placement of a contact lens;

FIG. 2A is a perspective view of the inner-working elements of the instrument, illustrating the eyepath for gross alignment and the three detector eyepaths for both fine alignment as well as actual keratometric measurements;

FIG. 2B is a schematic illustration of the principal light paths for measurement of the human eye showing infrared light sources adjacent the locus and detectors adjacent the eye;

FIG. 2C is an illustration of light paths similar to those illustrated with respect to FIG. 2B with measurement of a contact lens illustrated and the detector and light sources being reversed with the light sources adjacent the contact lens and the detectors adjacent the moving boundary locus (this particular configuration being preferred);

FIG. 2D is an expanded image of the light sources superimposed on the corresponding measuring areas of a human eye used for this invention;

FIG. 2E is an enlarged cross-sectional view of an emitter or detector;

FIG. 3A is a view of a patient's eye illustrating the interrogating detectors with the sources of light being used in the acquisition mode;

FIG. 3B is a view of the same eye illustrating sweeping of the three sources substantially simultaneously to generate the measurement of this invention, liberty being taken with the actual placement of the image of the moving boundary locus for ease of understanding;

FIG. 3C is a schematic illustrating the detector circuitry for identifying from each detector the particular light source being imaged;

FIG. 3D is a schematic of the analog to digital converter used in FIG. 3C;

FIG. 3E is a schematic of a filter utilized for signal recognition at the photosensors;

FIG. 4A is a side view detailed optical schematic illustrating the light paths used herein;

FIG. 4B is a patient's view of the instrument illustrating detector positioning as well as certain fixation targets which can be used;

FIG. 4C is a perspective view of the preferred detector;

FIG. 5 is an illustration of the moving boundary locus utilized with this invention, which moving boundary locus is typically registered to the detector by means of a real image relayed by reflection from the cornea or contact lens being measured;

FIG. 6 is a diagram of micro-processor logic that can be used with the light measurement system of this invention;

FIG. 7 is an illustration of a digital detector for detecting occultations in the presence of diffusely reflected light from the human iris;

FIG. 8 is a front view illustrating in a format similar to that shown on FIG. 2C with photodiscrete sensing elements being shown analyzing the sphere, cylinder and axis at three discrete points on the human cornea;

FIG. 9 is a section of the human eye illustrating the cornea without a lens placed thereon;

FIG. 10 is a view of the human cornea with a contract lens placed thereon for the purposes of illustrating the various refractive interfaces created thereby; and FIG. 11 is a block diagram illustrating the method of this invention for the fitting of contact lenses.

The following description is lengthy. First, the physical configuration of the unit is described. Then the moving boundary locus—which essentially is a rotating disk having light and dark areas of special, known shapes used to interrupt the light passing between the eye and a detector—is described. The measurement of the position of the beam using the moving boundary locus is described. Then computations exemplary of those which can be used to demonstrate the utility of the invention are set forth in the next two sections.

An electrical circuit schematic is discussed followed by a section on the disclosed computer flowchart and timing diagram.

Following the description of the keratometer, its used in obtaining a corneal map is set forth. Specifically, measurement of the eye in sphere, cylinder and axis at three spaced apart points is set forth. Thereafter, the parameterization of my invention resulting in the generation of an eye map is disclosed. Finally, the use of the eye map in fitting at least contact lenses is illustrated.

Physical Configuration

Referring to FIG. 2A, the optical portions of this keratometer are placed within a housing H. Housing H is mounted to a table T and given the degrees of movement generally illustrated in FIG. 1A. Generally, housing H is mounted on a pivotal mount 14 movable in azimuth indicated by arrow 15. Mount 14 in turn is movable on ball screws, belts or similar devices 16 for towards and away movement 17 relative to the patient P. Rack 16 on its own mount is movable in a side-to-side movement 19 on ball screws, belts or similar mechanisms 18.

Patient P registers his head and chin to a headrest 20 and chin rest 22. The forehead is registered to a headrest crossbar 25. In this position the eye E of the patient is registered for keratometric measurement. Degrees of movement are responsive to the outputs which will hereinafter be discussed. Since methods and apparatuses of effecting the illustrated degrees of movement of FIG. 1A are well-known to those having ordinary skill in the art, they will not further be discussed here.

Headrest 20 is typically rigidly mounted to the table T at a bar mount 28. It will thus be seen that the housing H is free to move with respect to the headrest 20. In such movement the housing will move about so that the eye E of the patient is properly addressed for keratometric measurement.

The present invention is also capable of measuring the curvature of a contact lens C. The mounting of such a contact lens C for reflective measurement of the inside radius of curvature is illustrated in FIG. 1B.

Bar 28 mounted to table T (not shown in the view of FIG. 1B) has the headrest removably mounted to a hole 30 in the upward portion of the bar. As here illustrated, the bar 28 includes a flat portion mounted to the table, an angularly and upwardly extending medial portion and a flat upper portion. The flat upper portion contains hole 30 and is the point to which both the headrest 20 and the removable contact lens mount 35 mounts.

The contact lens mount consists of a vertical rod 36 having an upper bar 37. Bar 37 has a V-shaped groove containing a rod 38. Rod 38 has a cylinder 39 on the end thereof, which cylinder is provided with a curved surface to which the contact lens C is mounted, typically on a fluid layer.

In operation, contact lens C is mounted to the surface 39 on the end of rod 38. Thereafter, rod 38 is placed within the V-shaped groove of bar 37. Bar 37 at attached rod 36 is mounted to the removable mount 35. Upon insertion of bar 37 into removable mount 35, reed switch 32 closes. As will hereinafter be made clear in the following description, reed switch 32 functions to reorder the logic within the apparatus. This recordering is required because the concave surface of the contact lens alters the optical path from light source to detector. It will be noted hereafter that the 90° spatial interval which has been chosen about the optic axis of the instrument allows this switching to occur by the addition of either an additional light source or additional detector.

It will be appreciated that the disclosed keratometer measures curvatures only within a preselected range. These curvatures (positive for the convex surface of eyes; negative for the concave surface of contact lenses) must be in a preselected range or measurement will be rejected.

Before proceeding further, and with reference to FIG. 2A, the major operative parts of the keratometer will be discussed. Thereafter, and with reference to FIG. 2B, the optical path utilized in examining an eye will be set forth. In FIG. 2B, this path will be described having the light sources adjacent the moving boundary locus and the detectors adjacent the eye.

Following this description, reference will be made to FIG. 2C. In FIG. 2C, the optical path generated for monitoring a contact lens will be discussed. Moreover, and with reference to FIG. 2C, the preferred embodiment having the light source adjacent the optical surface being examined (here the contact lens) and the detectors adjacent the moving boundary locus will be set forth.

In order that these matters may be easily understood, the contents of the keratometer within opaque housing H will first be discussed.

Referring to FIG. 2A, the opaque housing H is illustrated in schematic section. A brief explanation of the optics contained therein with respect to the eye E of the patient is illustrated.

Housing H includes four light sources 41, 42, 43 and 44. These light sources are typically infrared, have paired emitting sources and will be more fully set forth hereinafter. For the present, one of the light sources 43 will be explained in its full optical path. Such explanation will refer both to the side view of FIG. 4A and the perspective view of FIGS. 2A and 2B.

Light source 43 typically consists of two inner and paired point sources of light. These lights are focused through a lens in source 43 to a mirror 45. Mirror 45 merely serves to fold the light path and shorten the overall length of housing H. The invention will likewise work with the positions of the detectors and sources reversed as in FIG. 2C. The paired light receiving areas 41a, 41b are shown in FIG. 2E.

From mirror 45 the light from source 43 passes through focusing optics 46. From focusing optics 46 the light path is folded, first to a pyramid mirror 47 and thence to a convex mirror 48 where the light sources comes to a focus at an aperture stop 50.

From a real image of the sources at aperture stop 50 light passes through focusing optics 52.

Eye E of a properly positioned patient intercepts the light. With this interception, a virtual image of the light source is formed interior of the eye at a position dependent upon the radius of curvature of the cornea to be measured.

Moving Boundary Locus

Referring to FIG. 5, the configuration of the moving boundary locus is set forth. This moving boundary locus is described in my U.S. Pat. No. 4,182,572, issued Jan. 8, 1980, at FIG. 3A thereof. This patent is incorporated by reference into this specification. The disclosure of the patent may be summarized as follows:

A unitary light source is imaged through a prism array to generate a plurality of, preferably four, apparent light sources forming a point of origin for a discrete lens sampling light path. From each apparent light source, each discrete sampling path diverges to a relay lens system. This relay lens system relays and registers to a lens sampling interval discrete images of each apparent light source. The images may be registered to a correspondingly apertured lens sampling diaphragm against which suspect optics are placed for measurement. A moving boundary locus sweeps the light between each apparent source and the sampling interval with paired boundaries of differing slopes which produce non-ambiguous points of intersection with respect to time. After passage through the suspect optics at the sampling interval, light is passed to a photodetector having an overlying set of apertures, each aperture corresponding to one of the four apparent light sources. A lens pair functions as relay optics to focus a conjugate image of the light at the suspect optics to the overlying apertures at the detector. Light other than that passing through the suspect optics at the point of the images of the apparent light source is excluded. Moreover, a sampling aperture in combination with one of the lenses of the relay pair passes only that light with limited angularity substantially parallel to a selected optic path for each discrete light source. Light having an angularity other than the selected angularity is excluded from the conjugate image. Provision is made to fold the light paths to a C-shaped configuration to shield both extraneous light and electro-mechanical interferences from sensitive photodetector elements.

An exemplary claim of this patent is as follows:

1. In combination, means for emanating light from a discrete light emitting area; a moving boundary locus including at least one boundary for occulting said discrete light emitting area; a sampling interval to which suspect optics may be placed for deflecting light passing through said sampling interval; means for converging light from said light emitting area to a bundle of non-parallel light rays having a pupil located coincident with said suspect optics located in said sampling interval to which suspect optics may be placed for deflecting said light, said light diverging as deflected in a diverging bundle from said suspect optics at said sampling interval; a light path downstream from said sampling interval to receive at least a portion of said light from said suspect optics; and a photodetector fixed in space with respect to said downstream light path located within an area of expected excursion of said light from said sampling interval to detect changes of occultation of said light path by said moving boundary locus.

In the present invention, the moving boundary locus L used can be identical in configuration to that illustrated in my U.S. Pat. No. 4,182,572. Referring to FIG. 5 herein, moving boundary locus L is made of a disc of material such as glass or even metal. The disc is provided with two broad information areas. The first area is a border area 120 which defines disc rotation. The second area comprises an internal area 124 of the disc which occults the view of the light detectors to the virtual image of the light sources in the eye of the patient E. Border area 120 consists of a group of discrete notches for bar patterns 122 placed in a preselected angular spatial relationship around the periphery of the disc. In this case, they are placed at spatial intervals of 256 notches to the revolution. The function of the notches 122 is for precise rotational location of the disc. When this precise rotational location of the disc is identified in combination with the occultations of light to a detector from a light source, precise angular measurement of the position of the disc can occur.

Gross overall rotational reference is made to a missing notch at interval 121. By electronic recognition of this interval through time-sensing circuitry, precise rotational positioning of the locus L at the time of occultation can be determined.

It should be understood that border area 120 can consist of a number of embodiments. For example, a Baldwin type digitizer disc can be used to determine the precise rotational location of the moving boundary locus L. Such discs are manufactured by Baldwin Electronics, Inc. of Little Rock, Arkansas as a commercial item of manufacture.

It will be appreciated that the light path from each of the light sources 41–44 intersect the moving boundary locus L at respective areas 70–73. These areas are shown in broken lines on the disc as it is illustrated in FIG. 5.

Using the corneal surface of the eye E (see FIG. 2B), a real image of the moving boundary locus is registered to the detectors. Taking the case of detector $D_3$, a real image of the locus passes in front of the detector $D_3$ to effect occultation of any virtual image of the light source within the eye E. In other words, locus L is placed along the optical paths between the detectors and the light sources. As the moving boundary locus rotates, the light traveling along the various paths at areas 70–73 is sequentially interrupted by the opaque portions 140, 142.

Keeping in mind the projection of the real image of the moving boundary locus to the aperture of the detector $D_3$, it will be realized that the position of the virtual image of the light source 43 within the eye E can readily be determined with occultation. In explaining how such occultation theoretically works, attention will first be given to the parameters of the disc and a discussion of the boundaries between the opaque and transparent areas. Second, the function of how these areas work will be set forth. Finally, the general case for such a moving boundary locus will be explained.

Broadly, the rotating boundary locus includes two transparent areas and two opaque areas. Turning attention to the transparent areas 132, 133, each area includes a boundary which can be described by the equation $R = k\theta$ (for boundaries 134a and 134b) and $R = -k\theta$ (for boundaries 135a and 135b) where:

R is radial distance of a point on the boundary from center of boundary locus (in inches);

$\theta$ is angular distance of a point on the boundary from a reference axis (in degrees);

k is a constant, 0.017453.

In the subject specification, very precise values are given for constants. These values come from actual experiment. The reader will understand that different units can yield different constants.

Each of the boundaries 134a and 134b on one hand, and 135a and 135b on the other hand, are separated by a precise angular interval of 90° at any given radius. Thus, it can be seen that the transparent portions of the moving disk as they pass any one spot within area 124, pass light for one half of the time and do not pass light for the remaining one-half of the time, all this over one complete turn.

Referring to opaque portion 140, it will be seen that the opaque area gradually increases in occupied angular interval with movement away from the axis 141 of the rotating boundary locus. This is because the respective boundaries 134a and 135a occupy an increasing angular interval of the disk as the distance radially outward from axis 141 increases.

Portion 142 is of the opposite construction. Specifically, the angular interval between the curces 134b and 135b decreases with outwardly moving radial distance from the axis of rotation 141.

Measurement of Position of Beam Using the Moving Boundary Locus

Assuming that a beam passes through the disk at a distance r and an angle $\theta$, the passage of the beam can be intuitively understood before considering the more general case. Specifically, for changes of the distance r towards and away from axis 141, it will be seen that the time during which the beam is obscured by the respective opaque surfaces 140 and 142 can be determined. In the case of opaque surface 140, the longer the obscuration of the beam by the surface 140, the further away from the axis 141 will be the location of the beam. In the case of opaque surface 142, the shorter the obscuration of the beam, the further away from the axis 141 will be the beam. Thus, the opaque surfaces each provide discrete timed intervals which indicate the polar coordinates r of the beam away from the rotational axis 141.

Referring to the angle $\theta$ of the beam from axis 145, the average integrated time interval between the reference position of the disk and two opaque to transparent boundaries can be used to determine angularity. For example, by observing the boundaries 134a and 135a as they respectively occult a beam it will be observed that the angle subtended between detection of marker 121 and these obscurations will average to a value representing the azimuthal position of the beam about the axis 141. This azimuthal position can be measured with extreme accuracy. By relating this rotation interval to the precise rotational interval of the tracks 120, migration of the beam in angle $\theta$ can readily be determined.

It will be apparent that more than the preferred four boundaries here shown can be utilized. For example, six boundaries could be used. Likewise, the opaque and transparent portions of the boundaries could be reversed.

Having set forth the migration of the beam, the more general case can now be explained.

It should be apparent to the reader that the moving path of a boundary locus according to this invention can vary widely. For example, the moving path could be linear and comprise a series of boundaries all sequentially passing the area of expected beam excursion. Likewise, the boundary locus could be pointed on the exterior of a transparent revolving cylinder. Light could be deflected through the sidewalls of the cylinder with occultation of a beam occurring with boundaries painted on the cylinder sidewalls. It is to be understood that the rotational disk embodiment here shown is a preferred example.

The boundary here illustrated comprises successive opaque and transparent areas on the surface of the disk. It should be understood that absolutely transparent or absolutely opaque areas are not required for the practice of this invention. Varying surfaces can be used so long as the relatively transparent areas are capable of passing therethrough a beam of light which can be intercepted without appreciable degradation by a detector. Likewise, lights of various colors could be used in combination with color discriminatory filters. For example, a combination of lights and narrow band pass filters could be used to successively pass various beams. These beams, when passed, could be measured in timed sequence at a single detector plane.

The boundaries cannot be parallel to the intended path of movement of the boundary locus. In such a case, there would be no sweeping of the area of excursion and no detection of the beam.

It is required that the two boundaries be boundaries of distinctly different shape. This differing in angularity requires that each boundary sweep the area of intended beam excursion and that the two boundaries, when occultation occurs, form a common point of intersection. This common point of intersection can define the point of excursion of the beam.

Regarding the moving boundary locus, it is preferred that the boundary move at a known and constant speed. When moving at a known and reasonably constant speed, the equation for determination of the location of the beam can be reduced to one of time combined with knowledge of position from the marks 121 and 122. That is to say, by observing the time of respective occultations, precise location of the beam excursion can be measured. Once excursion is known, the resultant prescription can be obtained.

The particular configuration of the moving boundary locus illustrated in FIG. 5 is preferred. In actual practice, the boundary can have other configurations.

As a practical matter, it is important that at least two boundary contours be employed. The slope of one of these boundary contours must be algebraically larger than the other with respect to the direction of translation of the boundary across the light path. Such a slope gives the boundaries a non-ambiguous point of intersection, which non-ambiguous point of intersection insures accurate location of the beam within a suspected area of excursion, for example the area 70.

It has been found convenient that the slope not change its sign. If the slope is chosen so that a sign change occurs, it will be found that the resultant function is non-monotonic. That is to say, the value of one component producing the slope decreases instead of increases over the area of excursion. This produces difficulty of solution of the resultant equations.

Naturally, the boundary can be described with respect to polar coordinates—where the boundary is rotated as shown in the preferred embodiment; or Cartesian coordinates—where the boundary is merely translated by the light beams with the respective opaque and transparent areas defining boundaries described by the conventional X, Y description.

Where the boundary is one that rotates, the slope $d\theta/dr$ of one boundary must be algebraically larger than the other. Obviously, this is where translation occurs in the direction $\theta$.

Where the boundary is translated in the X direction in a Cartesian system, the slope $dx/dy$ of one boundary must be algebraically larger than the corresponding slope for the other boundary.

It is an important limitation that each boundary sweep over the expected area of excursion. Naturally, where the boundary does not completely sweep the expected area of excursion, the limitations of this general condition would not be met.

Referring to FIGS. 2A and 4A, it will be remembered that the light from each of the light sources impinges on the pyramid type mirror 47. In actual fact, pyramid mirror 47 is provided with a central hole or aperture 49. The mirror includes sloped surfaces, each sloped surface forming a surface from which the light forming image of the moving boundary locus near the detectors is reflected.

It will be remembered that the moving boundary locus L has its real image relayed by the cornea being measured to a position at or near the aperture of the detector $D_3$. Looking back through the detector $D_3$ onto the surface of the eye E, the virtual image of the light source 43 will be occulted. If one were to draw a diagram on the eve illustrating the projected photosensitive area of each detector and illustrate the occultation of all of the virtual images of the light sources by the real image of the moving boundary locus, one can generate a diagram that looks like FIG. 3B. The reader should understand however that FIG. 3B is a diagrammatic and schematic representation of the occultation of the virtual images of the light sources taking place and does not represent with complete accuracy images occurring at these points.

Specifically, in FIG. 3B a human eye E is illustrated. Eye E includes the optical axis 57 of this instrument impinging upon the eye. The pyramid mirror 47 creates quadrants of the eye onto which the light paths are projected. In the view of 3B, we see the locus superimposed upon a view of the eye. Thus, we see boundary 135b sweeping quadrant III at 135b'. Similarly, the boundary 135a sweeping quadrant II at 135a' and boundary 134a sweeping quadrant I at boundary 134a'.

Referring briefly to FIG. 5 and then FIG. 3B, it will be noted that another feature appears. Referring to FIG. 5, it will be seen that areas 70, 71 and 72 are formed about the locus L with spatial intervals therebetween. Specifically, a spatial interval sufficient to accommodate the drive shaft 143, of the moving boundary locus L is illustrated.

However, referring to FIG. 3B, it can be seen that the spatial interval between the respective imaging areas 70, 71 and 72 has been removed and now areas 70-72 essentially correspond to sectors I, II and III. This is a function of the pyramid mirror 47. This mirror acts to bring the respective images of areas 70, 71 and 72 into an overlapping real image area at the eye of the viewer. Thus, the real image of the spatial areas swept by the locus at the eye in fact overlap a small amount along the boundaries of the quadrants I, II and III.

As will hereinafter more completely appear, once each of the light sources is in registry with its own segment, further movement can and must occur to even more finely align the instrument. This movement includes more precise angular positioning as well as axial distance calibration. This movement occurs with respect to a mathematical parameter which is in effect nulled by further controlled movement of the instrument. In order that this parameter may be understood, the instrument measurement will now be discussed using the view of FIG. 3B; optical axis 57 will be assumed to be adequately centered upon the cornea of the eye E.

Referring to FIG. 3B, it will be remembered that the image of the locus L is focused to the eye E. At the same time, each of the detectors $D_1$, $D_2$ and $D_3$ is capable of viewing the eye. Some attention can be given to the light gathering properties of these detectors. A typical detector is illustrated in FIG. 4C.

Typically, the detector includes a lens 150 and an infrared detecting element 151. The lens and detecting element are spaced apart along an opaque housing 152.

The detector has a discrete solid angle of acceptance. This is defined by the detector 151 and the lens 150. The conjugate image of each detector element 151 is formed to and on the virtual image of the light source as it appears in the cornea of the eye E. This is shown as areas A, B and C on FIG. 3B.

With further reference to FIG. 3B, it will be remembered that an image of a moving boundary locus L is projected to the detectors. Further, it will be understood that the timing markings 120 (see FIG. 5) on the periphery of the disk enable the precise angular positioning of the disk with respect to an occultation to be determined. Knowing the shape of the boundaries of the locus L, one can therefore determine the R and $\theta$ position of each of the virtual images A', B' and C' with precision. This is set forth in equations which follow.

Exemplary Computations for Measurement of Curvature of Eye

The following mathematical equations are different in scope and extent to that material set forth in my U.S. Pat. No. 4,180,325, issued Dec. 25, 1979, entitled "Lens Meter with Automated Read-Out." It will be observed that with the following equations, only three points are used to determine readings in sphere, cylinder and axis.

It will be appreciated in reading the following equations that they are only suited for the keratometric exercise herein set forth. They are unsuitable and do not work with a lens meter.

Once the mathematical equations are understood, it is believed that programming can be arrived at by those having skill in the art by following the format of the exemplary progrm set forth in the above-referenced patent and adapting the programming to the equations set forth.

Although only three detectors $D_1$-$D_3$ are illustrated, it should be remembered that the location of the detectors and light sources can be reversed as in FIGS. 2B and 2C. Therefore, in FIG. 2B, elements $D_1$-$D_3$ are detectors while in FIG. 2C elements $D_1$-$D_3$ are light sources and elements 41-44 are detectors.

It should be noted that no image is projected into the upper quadrant of the eye, although that quadrant may be used when measuring contact lenses, to minimize upper eyelash interference. The use of relatively small, paired light sources or detectors for each path further reduces eyelash interference.

In the equation format given below, let $R_i$ $\theta_i$ be the position on FIG. 3B of a virtual image A', B', C' corresponding to the particular detector $D_1$–$D_3$. Let $d_j$ be the number of counts between two edge crossings for a given detector. In noting the moving boundary locus of FIG. 5, the reader will observe that there are four edges 90° apart at any crossing and thus each expression has four terms whereas we are only determining the position of three images.

In the solution of equations, we first need to determine the radius of the virtual image of the spots A', B' and C' at the physical plane of the boundary locus. This is given by the equations:

$$R_1 = \frac{k}{4}(d_3 - d_4 + d_2 - d_1) + 1.0000$$

$$R_2 = \frac{k}{4}(d_2 - d_3 + d_1 - d_4) + 2.5708$$

$$R_3 = \frac{k}{4}(d_1 - d_2 + d_4 - d_3) + 1.0000$$

Where:
$R_1$ is radial distance (in inches) of point A' from optical axis 57;
$R_2$ is radial distance (in inches) of point B' from optical axis 57;
$R_3$ is radial distance (in inches) of point C' from optical axis 57;
k is a constant, 0.017453;
$d_1$–$d_4$ are angular distance (in degrees) between reference mark 121 and consecutive edge crossings for a particular spot, A', B', or C'.

Similarly, we need to determine the angle from the axis 57'' of each of the virtual images A'–C'. This is given by the equations:

$$\theta_1 = 45° + \tfrac{1}{4}\Sigma d_j - 180°$$

$$\theta_2 = 225° + \tfrac{1}{4}\Sigma d_j - 180°$$

$$\theta_3 = 315° + \tfrac{1}{4}\Sigma d_j - 180°$$

Where: $\theta_1$, $\theta_2$, $\theta_3$ are angular distances clockwise (in degrees) between reference axis 57'' and points A', B', and C' respectively.

In the above equations, the constants naturally depend upon the particular shape of the boundary loci.

As is set forth in my above-referenced U.S. Pat. No. 4,180,325, locus L is equipped with 256 timing markers about its periphery (one of the markers being omitted to determine angular reference). Moreover, approximately 256 timing counts are made between the passage of each timing mark. This being the case, it is possible to establish the accuracy of a particular timing measurement by determining the deviation from zero of the checksums $T_1$, $T_2$, $T_3$:

$$T_1 = d_3 - d_2 - d_1 + d_4 - 360°$$

$$T_2 = d_2 - d_1 + d_3 - d_4$$

$$T_3 = -d_3 + d_2 - d_4 + d_1 + 360°.$$

Where:
$T_1$ is checksum for measurement of point A';
$T_2$ is checksum for measurement of point B';
$T_3$ is checksum for measurement of point C'; and,
$d_1$–$d_4$ are defined above.

A measurement is to be rejected if $T_1$, $T_2$, or $T_3$ is greater than some predetermined value.

Thereafter, each of the angular determined $\theta$ values is corrected by predetermined constants. As an example, the following constants for each of the determined $\theta$ values, $\theta_1$, $\theta_2$, $\theta_3$ have been used:

$$\theta_1 \rightarrow \theta_1 - 4.97°$$

$$\theta_2 \rightarrow \theta_3 - 4.62°$$

$$\theta_3 \rightarrow \theta_4 - 4.58°$$

It will be remembered that a pyramid mirror 47 is present in the optical train. Mirror 47 adds a distortion to the determined radius along radial components which are along the slope of the mirrors. Accordingly, the determined radius must be corrected for that component added by the slope of the mirror as follows:

$$R_{ill} = r_i \cos(\theta_i - \theta_{oi})$$

$$R_{il} = r_i \sin(\theta_i - \theta_{oi})$$

Where:
i = 1,2,3
$R_{ill}$ is component of $R_i$ along a line bisecting the particular quadrant;
$R_{il}$ is component of $R_i$ perpendicular to $R_{ill}$;
$R_i$ is radial distance of a spot from optical center 57;
$\theta_i$ is defined above;
$\theta_{o1} = 45°$
$\theta_{o2} = 315°$
$\theta_{o3} = 225°$ Once these corrections have been made, the real radii and angles must be determined as follows:

$$R'_{il1} = R_{il1}[1 - .021(R_{il1} - 1)]$$

$$R'_i = \sqrt{(R'_{il1})^2 + (R_{il})^2}$$

$$\theta'_i = \theta_{oi} + \sin^{-1}\left(\frac{R_{il}}{R'_i}\right)$$

Where:
$R'_{ill}$ is the corrected $R_{ill}$ component;
$R'_i$ is the corrected distance $R_i$;
$\theta'_i$ is the corrected angular position $\theta_i$.

Further, correction must be made for any magnification factor present in the disclosed optics as well as any distortions. The reader will understand that these are empirically determined terms so that the numerical values given here are actual constants used in practice which will have to be re-evaluated should the apparatus be practiced using another or alternate embodiments.

$R'_i$ as determined above is the spot distance as measured at the plane of the physical locus. As measured at the corneal plane, the corresponding distance $r_i$ is given by:

$$r_i = 0.0991 R'_i - 0.00142 R'^3_i$$

Thereafter, conversion of polar to Cartesian coordinates can be made. This conversion is as follows: convert to ($X_i$, $Y_i$):

$$X_i = R_i \cos \theta_i$$

$$Y_i = R_i \sin \theta_i$$

Correct for mirror angle and displacement resulting therefrom:

$$X'_1 = X_1 - k \quad Y'_1 = Y_1 - k$$

$$X'_2 = X_2 - k \quad Y'_2 = Y_2 + k$$

$$X'_3 = X_3 + k \quad Y'_3 = Y_4 + k$$

Where $k = 0.0235$

Once this has been done, computation of equivalent sphere ($S_1$), 0°–90° astigmatic component ($S_2$), 45°–135° cylindrical component ($S_3$), and error function $\chi^2$ ($S_4$) can then be generated. These equations take the form:
Form the sums:

$$S_1 = \frac{1}{X_2 - X_3} + \frac{1}{Y_1 - Y_2} \quad (S_{eq})$$

$$S_2 = \frac{1}{X_1 - X_3} + \frac{1}{X_2 - X_3} + \frac{1}{Y_3 - Y_1} + \frac{1}{Y_2 - Y_1} \quad (C_X/2)$$

$$S_3 = \frac{1}{X_3 - X_2} + \frac{1}{X_1 - X_2} + \frac{1}{Y_1 - Y_3} + \frac{1}{Y_2 - Y_1} \quad (C+/2)$$

$$S_4 = \frac{1}{X_1 - X_3} + \frac{1}{X_3 - X_2} + \frac{1}{Y_3 - Y_1} + \frac{1}{Y_1 - Y_2} \quad (\chi^2)$$

Where:
seq is equivalent sphere;
($C+/2$) is half the 0°–90° astigmatic component;
($C_X/2$) is half the 45°–135° astigmatic component;
($\chi^2$) is an error function.

Regarding equation $S_4$, two important points can be made. First, $S_4$ is typically analyzed to determine the desired distance calibration. This analysis involves a comparison of $S_4$ using first one set of light sources and then the other set of light sources utilized in point sources 41–43. Instrument movement occurs to change the values. When both determinations of $S_4$ agree, the instrument is axially positioned at the proper distance from eye E of the patient.

Second, if equation $S_4$ produces similar, and substantial non-zero values for each set of light sources, non-toric surfaces can be indicated. This value will vary with the particular construction. This value acts as a check for non-toric functions. That is to say, that where $S_4$ exceeds a certain empirically determined value, the measurement may be "flagged," indicating to the operator of the instrument that he has an eye E which is a candidate to be examined for non-toric surfaces.

The determined values $S_1$ through $S_3$ are scaled to produce readings of sphere and astigmatism (in diopters) by the following:

$$S = K S_1$$

$$C+/2 = -K S_3$$

$$C_X/2 = +K S_2$$

Where:

S is equivalent sphere in diopters;
$K = 1.8698$ and is an empirical constant;
$C+/2$ and $C_X/2$ are the astigmatic components in diopters.

Thereafter, these determined values of sphere and astigmatism can be corrected for incipient error by the following curve fit relations wherein the constants $a_0$, $a_1$ and $a_2$ are determined according to standard curve fitting procedures.

$$Y \rightarrow Y - [a_0 + a_1(S - S_0) + a_2(S - S_0)^2]$$

Where:
Y represents either S, $C+/2$, or $C_X/2$;
$a_0$, $a_1$, $a_2$ are constants particular to S, $C+/2$, and $C_X/2$;
$S_0$ is a preselected reference value of equivalent sphere.

Cylinder may then be found using simultaneous solutions of the following equations:

$$C+/2 = (C/2) \cos 2\theta$$

$$C_X/2 = (C/2) \sin 2\theta$$

Where:
C is total cylinder power;
$\theta$ is cylinder axis.

Finally, the result can be presented in conventional form giving the powers in two perpendicular axes: $S_{Rx1}$, the power along a direction normal to the cylinder axis, and $S_{Rx2}$, the power along the cylinder axis.

$$S_{Rx1} = S + C/2$$

$$S_{Rx2} = S - C/2$$

Where:
S is equivalent sphere;
C/2 is half the total cylinder power.

Having set forth with reference to FIG. 3B the actual measurement of an eye, the acquisition of an eye will now be discussed.

Exemplary Computations for Alignment of Keratometer with Eye

Referring to FIG. 2A, the optics by which gross acquisition of the eye E of the patient are acquired can now be set forth.

The keratometer housing H is provided with a direct eyepath by which an operator O (schematically shown) can view along a direct line of sight to the eye of a patient E. A light source 80 interior of housing H impinges upon a beam splitter 81. At beam splitter 81, the light source 80 has a virtual image which appears to be at or near the vicinity of eye E.

To aid alignment, especially in subdued light, light sources 83, 84 in the face of the instrument, shown in FIG. 4B, are turned on. These light sources are in turn visible as virtual images in the cornea of the patient's eye. The keratometer operator O registers the imaginary image of light source 80 to and typically between the virtual images of the light sources 83, 84 of the instrument face light sources in the eye of the patient E. When this registration occurs, gross alignment of the instrument is effected.

Once gross alignment of the instrument is effected, the optics of the instrument must then be used to effect fine alignment. Such fine alignment will be discussed once the light paths illustrated in FIGS. 2B and 2D and the circuitry of FIG. 3C is understood.

Referring to FIG. 2B, light emanating from the housing H is illustrated impinging upon an eye E. The eye E displays to such light a convex surface. Consequently, respective detectors $D_1$–$D_3$ receive light from sources 41-43. (See FIG. 2A).

The point has previously been made in FIG. 1A that the disclosed invention can just as well be used for measuring contact lenses C. Such measurement is illustrated in the schematic light train of FIG. 2C. In FIG. 2C, however, it will be remembered that the contact lens C is a concave surface. This being the case, light source 41 is imaged at detector $D_3$ and light source 43 is imaged at detector $D_1$. Light source 42 is not used. Source 44 is substituted for this light source and images at detector $D_2$.

It will be recalled that with respect to FIG. 1B, a microswitch 32 was attached. Microswitch 32 is switched upon the insertion of contact lens holder 35. This microswitch functions to switch the detector alignment to the circuit logic as hereinafter set forth when a contact lens C is substituted for the eye E. It will be realized this is optional (a simplification) as the correspondence between sources and detectors also identifies contacts, and which contact lens surface is exposed.

It will be appreciated that light sources 41-44 and detectors $D_1$–$D_3$ are interchangeable. As of the moment of filing of this patent application, I have not yet identified the preferred location of light sources and detectors insofar as their interchangeability is concerned.

Additionally, it may be desired to measure optical curvature of the convex portion of a contact lens. It will be appreciated that the instrument herein could be so used and so adapted.

Having set forth the light paths and the respective switching of detectors, attention can now be directed to the light sources.

Referring to FIGS. 2C and 2D and describing the disclosed invention wherein high intensity light sources are placed at positions $D_1$, $D_2$, and $D_3$ adjacent the contact lens C, the detectors placed at positions 41-44 can be described. Each of these detectors and their alignment is schematically illustrated in FIG. 2D. The following explanation occurs with the image of the detectors being schematically relayed to the eye E schematically shown in FIG. 2D.

With reference to FIG. 2D and the detectors schematically there illustrated, detector 41 comprises two light receiving areas 41a, 41b. These photosensitive elements are sensitive in the infrared and aligned in side-by-side relation along a first oblique axis 90.

Detector 42 includes two side-by-side light photosensitive areas 42a, 42b. These respective infrared light receiving areas are aligned along a horizontal axis 91. Detector 43 includes two spaced apart light receiving areas 43a, 43b. These respective light receiving areas are sensitive in the infrared and aligned an oblique axis 92. The use of infrared light to measure the corneal surface of the eye avoids complications of instrument measurement which could occur where the eye—which is sensitive to visible light—has visible light suddenly impinging upon it resulting in squinting, blinking or other movement.

Referring to FIGS. 2B-2D, it will be understood that the paired light sources shown in FIG. 2B or the paired light detectors shown in FIG. 2C at FIG. 2B can be used alone or in combination to determine the axial or Z spacing of the instrument from the human eye. This spacing can be determined in two different ways.

First, and using for example paired photosensitive areas 41a, 41b, these respective paired surfaces act in a manner not unlike split-image range finder in a 35 mm camera. Specifically, by having the moving boundary locus L measure the optical center of each of the sections of the paired photosensitive areas 41a, 41b, a rather precise distance spacing of the eye E from the housing H can be determined. The same principles used in split-image range finders by using optically active and differing portions of a camera lens, the axial distance to the eye can be measured. Assuming that the eye does not move appreciably between the measurement occurring on surface 41a and the measurement occuring on surface 41b, by detecting the optical center and observing for shifts, one may determine proper distance spacing.

As a practical matter, the eye is always undergoing movement. At a minimum there is the rapid saccadic panning movement of the eye which panning saccadic movement makes desirable a quantification of any shifting of the optical centers detected by the instrument. Accordingly, and in order to minimize utility to the optical paths which I have disclosed, I have developed a mathematical relationship for determining distance, $S_4$, defined above.

It is emphasized that the mathematical relationship that I have hereto set forth for the quantity $S_4$ requires that each light path have two photo-distinct portions. For purposes of the analysis here it does not matter whether these surfaces are photo-emitters or photo-detectors. Hence, I will refer to these side-by-side areas as "photo-distinct" to cover both emitters and detectors.

Each of the two side-by-side photo-distinct areas must be set in spaced apart relation. Moreover, the axes 90, 91 and 92 must all be at differing angles with respect to one another. Preferably, the alignment is such that axis 90 is oblique, axis 91 horizontal and axis 92 oblique. Oblique axes 90, 92 intersect normally, one to the other. The sources 42a and 42b can optimally be somewhat further spaced apart as shown in FIG. 2D although this is not required. This is preferably done by a factor of about $\sqrt{2}$. In the event that four (4) channels are used, variable separation is not preferred.

As will hereinafter be set forth, the occultation of the paired photo-distinct areas 41a, 41b, 42a, 42b and 43a, 43b occurs so as not to shift the observed optical center when the eye is optimally positioned. When the eye is out of position, a shift of the observed optical center occurs. Before this can be set out to the reader, a schematic of the circuitry for this invention must be set forth.

Referring to FIG. 3C, respective photo-distinct areas 41a, 41b, 42a, 42b, 43a, 43b, 44a and 44b are illustrated here as light emitting sources or areas. Each of these light sources is infrared and includes a first light emitting diode and a second light emitting diode. The particular alignment necessary for the practice of the invention and set forth in FIG. 2B.

Circuit Schematics

Referring to the schematic of the circuit diagram at FIG. 3C, it can be seen that an oscillator A, through a driver can drive through switch matrix 101 either a light source 41a, or a light source 41b dependent upon the polarity of LED control switch 102. Likewise, oscillator B can drive light source 42a or 42b and oscillator C can drive light source 43a or 43b. It will be appreciated that the disclosed oscillators will operate at distinct and separate modes. Oscillators A, B and C have three discrete frequencies of oscillation.

Referring to the embodiment shown in FIG. 2B, it will be remembered that light sources 41a and 41b are incident upon detector $D_1$. Likewise, light sources 42a and 42b are incident upon detector $D_2$. Similarly, light sources 43a and 43b are incident upon detector $D_3$.

It is necessary that each of the detectors $D_1$ through $D_3$ be sensitive to determine which light source is incident upon them. Switching network 101 is provided with a switching pulse 100. Pulse 100 causes the output from oscillators A–C to step from light source to light source. Similarly, LED control switch 102 is provided with a switching pulse 104a for switching between the dual light sources 41a, 42a and 43a to 41b, 42b and 43b.

Detectors $D_1$–$D_3$ are connected to preamplifiers 104–106 respectively. Detectors $D_1$–$D_3$ put their respective outputs through amplifiers 104–106 to frequency selective phase detectors 111, 112, 114, respectively. Oscillators A–C also provide their output to detectors 111, 112, 114, respectively.

As noted above, switch pulse 100 causes matrix stepping between the respective signals from the respective oscillators to drive the respective light sources with differing frequencies. The particular light source signals incident to detectors $D_1$, $D_2$ and $D_3$ can be identified by comparing the frequency of the signal received by the particular detector at a particular time with the frequencies of the oscillators. Note that these signals would come from any of the light sources 41a, 41b, 42a, 42b, 43a, 43b (or 44a and 44b as set forth hereafter) on any single detector. Once the light sources are identified at the comparator, digital logic can cause the keratometer to move from a position of gross alignment to exact positions for keratometric measurement. This is possible based upon the $R-\theta$ relationship discussed with reference to FIG. 5. Thereafter, and as set forth with respect to the logic illustrated in FIG. 6, actual measurement of the eye can occur.

Having set forth the circuitry for recognition at each sensitive quadrant of the discrete point sources of light, and having described how gross registration of the housing H occurs, the actual acquisition of the eye E of a patient can be described by first referring to FIG. 2B and thereafter to FIG. 3A.

In FIG. 2B, it will be seen that the three active detectors $D_1$, $D_2$ and $D_3$ address the eye at an angle in the order of 20°. The light sources 41a–43b impinge upon the eye along the optical axis 57 of the instrument. It will be remembered that the cornea of the eye E is a convex surface and we in effect want the mire formed between the images of the light sources A', C' and B' to impinge about a pole of the eye coincident with the optical axis 57 (see FIG. 2). Referring to FIG. 3A, a gross alignment is assumed that has left the housing H with the optical axis 57' below and to the right. Consequently, the center of the illuminating areas of the light sources A', B' and C' will have moved below and to the right.

Where gross alignment has occurred, areas of detector sensitivity of detectors $D_1$, $D_2$ and $D_3$ will remain substantially unchanged. These detector areas A, B and C will remain substantially on the same quadrants of the eye.

Referring specifically to the view of FIG. 3A, it can be seen that light source C' is incident upon detector area B in this type of misalignment. With appropriate switching of the circuitry of FIG. 3C, detector $D_2$ in monitoring segment B of the eye will soon detect that sources 43a, 43b are been seen. Comparator 112 will output a signal that it has recognized image C' from light sources 41a in its quadrant. Translation of the overall instrument can then remotely occur by moving the keratometer illustrated in FIG. 1A in the direction of arrows 15, 19.

The reader will appreciate at this point, that two methods of instrument alignment have been set forth. First, and with respect to logic of FIG. 3C and the diagram of FIG. 3A, alignment of the instrument along the X and Y axes have been demonstrated. Secondly, and with respect to FIG. 2D, a system of detecting optical shifts in the disclosed optical centers of faced sources or detectors has enabled positioning of the instrument towards and away from the patient or along "the axis". Thus, there has been described thus far an automated positioning of the instrument.

It will be apparent to the reader that in moving from the alignment shown in FIG. 3A to that shown in FIG. 3B, instrument panning will occur to register the light sources A'–C' in quadrants I–III. However, registration may move so that the light sources are within the proper quadrant but not properly registered. Such a registration of light sources is illustrated with the optical axis being shown at 57" and light sources A", B" and C" in their respective quadrants I, II, III. In this case, it will be remembered that by using the equations for R and $\theta$ previously set forth, measurement of this lack of alignment may be easily made. Further instrument movement can occur until the alignment of the optical position shown at FIG. 3B occurs.

Computer

FIG. 6 sets forth the logic and computer hardware which the preferred embodiment herein contains.

The electronic circuitry of this invention includes four logical steps. First, monitoring of the rotational position of the rotating boundary locus L occurs. Secondly, recordation of occultations (typically by interference from a digitally produced intensity curve) as they occur at the photodiode D occurs. Third, the circuitry computes the angular interval of the infrared occultation. This is typically done to an accuracy of about 1 part in 50,000 of the total rotation, or 2/100,000ths of the total rotation. Finally, these angular values are computed to spherical power, cylindrical power and axis and position. These computed values are presented to the operator by either a light emitting diode (LED) display or printout.

Referring to FIG. 6, the standard parts of an electronic computer are shown. Particularly, a central processing unit (or CPU) 200, designated as Chip 8086, manufactured by Intel Corporation of Santa Clara, Calif. (hereinafter Intel) includes a system clock 201 (Intel 8224). The clock 201 is used for driving a position counter 202 (National Semiconductor chip 163 of Sunnyvale, Calif).

The CPU 200 inputs and outputs through a bus control 208 (Intel 8228). Bus control 208 functions to align the various inputs and outputs for circuit interrogation, computation and output.

A read only memory (ROM) 202 (Intel 2708) contains the program for the central processing unit 200.

Read write memory (RAM) 204 (Intel 8111) stores for retrieval various quantities read partially computed and fully computed by the detectors D.

An address bus 207 and a data bus 208a function to move data throughout the system. Standard computer components such as printer interface and printer 212 and a display keyboard interface 211, including a display and keyboard, are connected. Since these are standard state-of-the-art items, they will not be further discussed herein.

Referring to the moving boundary locus L as schematically shown on FIG. 6, it will be appreciated that three paired and separate outputs are received. As set forth herein, photodiode and amplifier-buffer assembly 210 monitors the counts of each of the notches 121 as they pass. This photodiode gives a rotational reading of the moving boundary locus L. Similarly, each of the areas of the photodiode $D_1$, $D_2$ and $D_3$ has a discrete output from the central area 125 of locus L.

Each of these optical outputs from the respective photodiodes included in 210 are buffered. This is accomplished by a double amplifier which includes a current to voltage amplifier and then one or more simple voltage amplifiers connected in series. The output signal is conventionally provided with reduced impedence which is less subject to noise interference.

It is necessary to note when one complete rotation of the boundary locus L occurs. This can be accomplished by either omitting a mark (as shown in FIG. 5) or alternately having a mark a double thickness. In the illustration shown in FIG. 5, omission of a mark occurs.

Regarding the inference of the light intensity curve and over that logic which I have previously disclosed, one problem peculiar to corneal measurements is present. Specifically, where a light such as the infrared lights of my invention are utilized, corneal reflection necessary for keratometric measurement and diffuse reflected iris illumination may simultaneously occur. In the case of the latter iris illumination, it will be appreciated that the light produced thereby is extraneous. This being the case, provision must be taken to screen out the iris illumination.

It will be appreciated that this iris illumination will vary. For example, in the case of brown eyes, the background illumination may differ from that of bluer eyes.

Referring to FIG. 7, a plot of illumination versus time is illustrated. Specifically, background iris illumination is illustrated by the line 300. It is noted that it has a variable magnitude and is present whether or not occultations occur.

The broken line 301 illustrates the infrared reflection from the eye which is a product of the occultations of the moving boundary locus. This produces a bell-shaped curve which gives a tell-tale indication of illumination.

Adding these two curves together, we get a composite curve, such as 302. The requirements for accurate measurement include pinpointing those portions of the curve having a rapid change in slope, such as point 303, 304, 305, and 306.

Although optical means, such as reduced sampling sectors in the moving boundary, may be used to reduce iris effects, I propose to locate these points by digital filters. Specifically, the development of light intensity is continuously monitored by the disclosed logic. In this monitoring (schematically shown along composite curve 302 as mark points "X"), the logic examines the intensity with respect to time. Where points of curvatures are located, indications are made. By appropriate and subtractive logic, the crossing of the curves of the composite curve 302 with a medial line 310, can be observed. The equations previously set forth can then be solved, using the data of equation 310.

Remembering the logic previously illustrated with respect to FIG. 3C and referring specifically to FIG. 3D, a phase detector useful with this invention is illustrated. Specifically, the input signal to a typical phase detector (111, 112, 114) is received and routed to a comparator 301A. Comparator 301A receives a second signal. This signal comes from a 12-bit up-down counter 302A through a digital-to-analog converter 303A. The comparator 301A compares a signal 304A to a photosensitive element. The output of the comparator is fed back to the up-down control. From the feedback to the up-down control, the output of the 12-bit up-down counter 302A passes to appropriate gating 305A with output at 306A to the CPU data buss as indicated at 306 on the schematic diagram of FIG. 6.

The signal into this circuit has the intensity of the solid line 310A at the lower righthand corner of FIG. 3D. Output 306A at the gate 305A follows the illustrated square wave form which by interaction of the comparator and feedback to the 12-bit up-down counter tracks digitally the bell-shaped curve 310A.

It is important that the filters reject signals out of phase with the respective oscillators. Specifically, a simultaneous rectifying filter is illustrated in the view of FIG. 3A. Broadly, a double-pole double-throw switch 320 is thrown at the frequency of the oscillator at input 321. The switched output of double-pole double-throw switch 320 passes through a differential amplifier 322 with output 324.

Where the signal in line 323 is in phase with the reference frequency, the system in conjunction with the differential amplifier 322 reverses the phase of the signal for each half cycle of reference frequency. A signal at the same frequency and in phase with the oscillation will appear at the output as a positive DC level. This positive DC level will pass the low pass filter 325 and go on for further processing.

Where the signal is out of phase with the oscillator, the switch, in conjunction with the differential amplifier, again reverses the phase for each half cycle of the reference frequency. Here however the signal will not be in phase. The result will be that those portions of the signal out of phase will be reversed and cancel those portions of the signal which are in phase. There will result a blocking of out of phase signals.

I will not further discuss switching of the logic upon the insertion of a contact lens. Such logic switching is believed to be well within the skill of those having skill in this art.

Detecting the Corneal Shape

Referring to FIG. 4B, it will be observed that fixation lights 500, 501 and 502 are in the face of the instrument. Typically, these lights will assign fixation to the patient. The patient will be told to view an illuminated light while the keratometric measurement is being taken. Naturally, lights 500–502 will only be illuminated one at a time.

Preferably, the lights have angularity assigned to them. The angularity can be in the broad range of 5° to 22°, the intermediate range of 10° to 15° or the narrow range of 12° to 14°.

In accordance with the foregoing description, there will occur at the respective points 500', 501', 502' the measurements specifically described. Comparing the view of the eye in FIG. 8 to the view of the eye in FIG. 2B, it will be immediately seen that the photodiscrete elements in FIG. 8 are vastly reduced in size. These photodiscrete elements are more nearly the size actually used in my keratometer. Specifically, the typical corneal diameter of the human eye is on the order of 12 mm. My photodiscrete elements cover an area of approximately 3 mm in diameter. Thus and with the fixation that I set forth, discrete measurements along the eye can occur.

It should be further noted that my measurements occur typically along a horizontal axis 503'. Preferably, I do not measure along other than a horizontal axis so that interference with the eyelashes may not occur.

It will also be observed that my method of computation has a surprising result. By use of measurement along a straight line, I am able to predict with some accuracy the corneal shape above and below the axis 503'. That is to say by scanning along such an axis, I get a determination of the overall shape and slope of the human eye well outside the line of scan.

Referring to FIG. 9, a sectional view of a human eye at the vicinity of a cornea 510 is shown. Specifically, and with reference to FIG. 9 it will be noticed that there is one air cornea interface 511 at which refraction occurs. Interiorly of the cornea and at lens 512, conventional refraction occurs for focus on the retinal plane of the eye in the vicinity of fovea 514 and the retinal plane 515.

Having set forth this much, an eye E similar to that shown in FIG. 9 is shown at FIG. 10. Here, however, the eye E has fitted thereon a contact lens 520.

It is instructive to consider the number of additional refractive interfaces that a contact lens can introduce. First, there is the conventional corneal interface 511. It will be appreciated that the mere presence of the contact lens 520 can have an effect at altering and/or changing the shape of the interface 511.

Secondly, and trapped between the contact lens 520 on one hand and the corneal surface 511 on the other hand there exists a tear layer 518. Tear layer 518 can have dimension and furthermore can have the requisite rate of change of dimension so that it becomes a very effective refractive interface. For example, as is known in the contact lens art and when a hard lens is present, this interface can be relied upon to produce astigmatism opposite it in typical effect to astigmatism afflicting the eye. It may be realized that this sort of correction of astigmatism at the cornea will not affect other astigmatism present in the eye such as that which may be resident in the lens 512 or on the retinal plane 515. Accordingly, the accurate determination of the depth of the tear layer and its optical effect may have importance.

Given that increased information in regard to corneal shape is a desirable goal, consider the possible ways in which corneal shape might be characterized. Two types of parameters come to mind—those that are primarily of theoretical interest in providing an improved description of the corneal shape and those which might be considered to have primarily a practical or clinical value in that they are an aid in contact lens fitting procedures. Naturally, some corneal parameters will be important on both counts. The list below represents in general terms the kind of additional information that can be expected.

1. Central "k" readings;
2. A measure of departure from circular cross sections;
3. A measure of alignment or positioning of the axis of symmetry of the cornea;
4. Detection of corneal irregularities;
5. Corneal diameter;
6. Vault height of the cornea (over the scleral extension);
7. "Cap size"; and
8. Corrected apex "k" readings.

These classes of corneal information have been characterized in a very general form. In actually arriving at a specific means of describing these corneal shape factors, it is necessary to arrive at some kind of compromise between the extent and detail of corneal information and the burden on both the patient and the doctor (or the technician, if the measurements are by a technician).

An overly complex examination places a burden upon a patient which can detract from the examination in two ways. First of all, the attention span varies greatly from one patient to another. The ability to successfully carry out a complex corneal measurement is enhanced as the measuring process becomes shorter and simpler. And, of course, the patient tires less. For instrumentation designed to make corneal measurements by a technician, it is probably preferable to maintain as simple and as objective a measuring procedure as possible. This implies a minimum of technician skill in arriving at the measurements. Such operations as retracting the upper or lower eye lid for any substantial fraction of the patients should be avoided. This type of manipulation is not only an inconvenience to the technician and the patient, but also has the potential of inducing significant changes of corneal shape. And finally, the matter of too much information vs. too little information is a factor of importance for the doctor. Overly detailed information on the corneal shape may confuse the basic characterization of the corneal shape through an over abundance of parameters which are unintuitive and difficult for the doctor to interpret. Inasmuch as it is probably impossible to devise any comprehensive, numeric description of every possible corneal shape, it becomes a question of finding the most effective and intuitive means of abstracting the available data to make the data more manageable and more easily interpreted by the doctor.

This balance between complexity of characterizations of the corneal shape and difficulty of measurement and interpretation has resulted in the following specific list of suggested corneal shape parameters.

1. Central "k" readings, mm. or diopters;
2. Corneal shape factor ($\epsilon$);
3. Corneal decentration distances ($\Delta_s$, $\Delta_t$, $\Delta_p$);
4. Chi-square values for individual corneal measurements and for fits of corneal measurements to an overall corneal shape;
5. Estimated vault height, mm.;
6. Cap size, mm.; and
7. "k" readings, transposed to the corneal apex and corrected, mm. or diopters.

Of these parameters, the last three are derivable from the first three but will be included as a matter of convenience.

The analysis of corneal shape through the combination of several keratometer measurements could be divided into two parts. Part I is each individual corneal measurement complete with its estimate for sphere and cylinder components, plus goodness of fit checks in the form of an $\chi^2$. For a 4-point keratometer measurement using full information in each of the four sample areas, the $\chi^2$ can be a "3c" $\chi^2$. For keratometer measurement employing full information from three sampling areas the $\chi^2$ is a "1c" fit (this latter method is preferred). Attention will be directed now toward combining individual measurements with the measurement values at each individual fixation angle assumed to be given.

The mathematical analysis of the cornea shape takes place as a sequence of analysis processes. First, the reflective deflections for one small area of cornea are distilled into a set of curvature measurements along with a goodness of fit parameter. Then, several such setss of curvature measurements taken at several corneal locations are reduced to a set of adjusted, idealized curvatures, i.e. fitted curvatures. Then, these fitted values are used to create intermediate parameters, and these parameters are then combined to produce the final corneal shape parameters.

Subject to several assumptions, it is conceivable that corneal shape factors could be estimated based on just a central "k" reading and one peripheral reading. However, the mathematical treatment of this abbreviated corneal measurement will be skipped over in favor of what will be termed the three-point corneal measurement. The reason for the preference of the three-point corneal measurement lies in the fact that not only the corneal shape factor can be determined, but also the corneal decentration distance $\Delta_s$ and $\Delta_t$ can also be determined.

The more detailed mathematical treatment of the three-point method which follows will require establishing a few mathematical conventions. The observed curvature measurements will be designated by $x_i$, as defined in the chart below:

$x_0$ central, perpendicular to sampling line
$x_1$ central, parallel to sampling line
$x_2$ nasal, perpendicular to sampling line
$x_3$ nasal, parallel to sampling line
$x_4$ temporal, perpendicular to sampling line
$x_5$ temporal, parallel to sampling line
$x_6$ central, oblique to sampling line, astigmatism component
$x_7$ nasal, oblique to sampling line, astigmatism component
$x_8$ temporal, oblique to sampling line, astigmatism component.

Optimized estimates for $x_0$ through $x_8$ are designated by $f_0$ through $f_8$ (fitted values). The fitting procedure deals with the data as two sets. The first set consisting of $x_0$ through $x_5$, is dealt with in the following manner.

A chi squared estimate is employed, subject to the following constraints:

$$3(f_0-f_2)-(f_1-f_3)=0$$

$$3(f_0-f_4)-(f_1-f_5)=0$$

These constraints are simply a mathematical statement of the "three-to-one" rule mentioned earlier.

The rule is applied separately for nasal and temporal measurements to allow for the effects of moderate corneal angular decentration. This is only approximately justified, as is the "three-to-one" rule itself.

Subject to the above mentioned constraints, the form of the chi-square function is as follows:

$$\chi^2 = \sigma^2\{(x_0-f_0)^2+(x_1-f_1)^2+(x_2-f_2)^2+(x_3-f_3)^2 + (x_4-f_4)^2+(x_5-f_5)^2\}$$

The fitted values are determined by the following relations:

$$f_0 = 1/30(12x_0+6x_1+9(x_2+x_4)-3(x_3+x_5))$$

$$f_1 = 1/30(6x_0+28_1-3(x_2+x_4)+(x_3+x_5))$$

$$f_2 = 1/30(9x_0-3x_1+12x_2+9x_4+6x_3-3x_5)$$

$$f_3 = 1/30(-3x_0+x_1+6x_2-3x_4+28x_3+x_5)$$

$$f_4 = 1/30(9x_0-3x_1+12x_4+9x_2+6x_5-3x_3)$$

$$f_5 = 1/30(-3x_0+x_1+6x_4-3x_2+28x_5+x_3)$$

$$\chi^2 \text{ two degrees freedom} = 1/10\sigma^2(\tfrac{2}{3})(a^2+b^2-ab)$$

$$a=3x_0-x_1-3x_2+x_3,\ b=3x_0-x_1-3x_4+x_5$$

The corneal shape factor information as well as part of the corneal orientation information is contained in the measurements $x_0$ through $x_5$, while the oblique asigmatism measurements $x_6$ through $x_8$ contain the remaining information regarding corneal orientation. In fitting this data, it is beneficial to allow for corneal decentration perpendicular to the sampling line. This accomplished through the use of the following constraint relation:

$$2f_6-f_7-f_8=0$$

A chi-square is then defined as:
$$\chi^2 = 1/\sigma^2[(x_6-f_6)^2+(x_7-f_7)^2+(x_8-f_8)^2]$$

with fitted values determined by the following relations:

$$f_6 = \tfrac{1}{3}(x_6+x_7+x_8)$$

$$f_7 = (\tfrac{1}{3})x_6+(5/6)x_7-(1/6)x_8$$

$$f_8 = (\tfrac{1}{3})x_6-(1/6)x_7+(5/6)x_8$$

$$\chi^2 \text{ one degree freedom} = \frac{(2x_6 - x_7 - x_8)^2}{6\sigma^2}$$

After having arrived at this set of fitted curvature values, these "f" values may be manipulated to arrive at the corneal shape parameters defined earlier. The chart below is a comprehensive collection of relations for intermediate values and final shape parameter estimates based on these "f" values:

Part I: Intermediate Results $\epsilon_{m3}\eta^2,\ \epsilon_{m5}\eta^2,\ \epsilon_{T2}\eta^2,\ \epsilon_{T4}\eta^2$ defined by $$\frac{1-\epsilon_{m3}\eta^2}{(1+\epsilon_{m3}\eta^2)^2} = 1 - \frac{2(f_1-f_3)}{f_0+f_1}$$

$$\frac{1-\epsilon_{m5}\eta^2}{(1+\epsilon_{m5}\eta^2)^2} = 1 - \frac{2(f_1-f_5)}{f_0+f_1}$$

$$\frac{1}{1+\epsilon_{T2}\eta^2} = 1 - \frac{2(f_0-f_2)}{f_0+f_1}$$

-continued $$\frac{1}{1 + \epsilon_{T4}\eta^2} = 1 - \frac{2(f_0 - f_4)}{f_0 + f_1}$$

$$\epsilon_N\eta^2 = .9\epsilon_{m3}\eta^2 + .1\epsilon_{T2}\eta^2$$

$$\epsilon_T\eta^2 = .9\epsilon_{m5}\eta^2 + .1\epsilon_{T4}\eta^2$$

$$\epsilon\eta^2 = \tfrac{1}{2}(\epsilon_N\eta^2 + \epsilon_T\eta^2)$$

$\epsilon\eta^2$ is a shape factor. This factor combines the overall shape of the eye with the magnitude of the offaxis displacement from the "summit" or "peak" of the cornea.

$\eta^2$ defined by $$\frac{d\xi}{d\eta}\bigg|_F = \left[\frac{\left(\dfrac{\eta}{1+\epsilon\eta^2}\right)^2}{1 - \left(\dfrac{\eta}{1+\epsilon\eta^2}\right)^2}\right]^{\tfrac{1}{2}} =$$

geometric constant, the tangent of the angle the surface normal at the point of measurement makes with the apical surface normal.
One can also write $\eta^2/(1 + \epsilon\eta^2) = K_1$ $$K = \frac{\left(\dfrac{f_0 + f_1}{2}\right)}{.3375 \times 10^3} \; (\text{mm}^{-1})$$

Part II: Corneal Parameters

1. Central "k"

$$\text{Equivalent Sphere} = \frac{f_0 + f_1}{2} = \text{Seq.}$$

$$0\text{-}90 \text{ Astigmatism} = \frac{f_0 - f_1}{2} = A_{0\text{-}90}$$

(+ cyl. at 0° ⟶ $A_{0-90} > 0$)

$$45\text{-}135 \text{ Astigmatism} = f_6 = A_{45\text{-}135}$$

(+ cyl. at 45° ⟶ $A_{45-135} > 0$)

The central k readings thus give the power in sphere, cylinder and axis of the "peak" and/or "summit" of the cornea.

2. Corneal shape factor; $\epsilon$ $$\epsilon = \frac{\epsilon\eta^2}{\eta^2}$$

The corneal shape factor $\epsilon$ gives a measure of the departure from a true sphere of the corneal surface. For example, if the corneal surface were spherical, the value would be 0. In actual fact, a flattening of the eye occurs which gives a value of 0.2 as a typical result found for this parameter.

3. Apex position; $\Delta_S$, $\Delta_T$, $\Delta_P$ $$\Delta_T = \frac{-\epsilon_N\eta^2 + \epsilon_T\eta^2}{4\epsilon\eta K} \quad \text{(+ if visual axis is temporal of apex)}$$

$$\Delta_S = \tfrac{1}{4}\epsilon\eta K \left[\frac{f_7 - f_8}{\left(\dfrac{f_0 + f_1}{2}\right)}\right]\left[1 + \left(\frac{\Delta_S K}{\eta}\right)^2\right]^{-1} \quad \begin{array}{l}\text{(+ if visual}\\\text{axis is super-}\\\text{ior of apex,}\\\text{right eye)}\end{array}$$

$$\Delta_P = K_2/4\epsilon\eta k \approx \left(\frac{.2}{43}\right)\frac{1}{4\epsilon\eta k} \quad \begin{array}{l}\text{(expected precision}\\\text{of }\Delta_T, \Delta_S, K_2 \text{ is an}\\\text{empirically determined}\\\text{precision constant)}\end{array}$$

These figures are a measure of the displacement of the peak with respect to a line of sight. $\Delta_T$ is horizontal, $\Delta_S$ vertical with $\Delta_P$ a measure of the uncertainty of locating this summit value.

4. Cap size—1 diopter level, diameter in mm $$D_{cap} = \frac{2}{k}\left[\frac{1}{\epsilon}\frac{(2-3\text{ Seq.}) + (9(\text{Seq.})^2 - 8\text{ Seq.})^{\tfrac{1}{2}}}{2(\text{Seq.} - 1)}\right]^{\tfrac{1}{2}}$$

5. Vault height (mm over a 25 mm sclera)

$$V = H_{(\epsilon)} \, 1/k - \left[\frac{25}{2} - \left[\left(\frac{25}{2}\right)^2 - \left(\frac{.768149}{k}\right)^2\right]^{\tfrac{1}{2}}\right]$$

$$H_{(\epsilon)} = .3596 - .1902\epsilon + .1115\epsilon^2$$

6. Corrected central "k"

$$\text{Seq.} = \text{Seq.}\left(1 + \frac{\epsilon\eta_m^2}{1 - \eta_m^2}\right) = \text{Seq.}(1 + k_3 S)$$

where $\eta_m$ is the surface tangent at the corneal measuring areas, and $k_3$ is the resulting computational constant, typically 0.036.

7. Goodness of fit $\chi_{2D}^2$ and $\chi_{1D}^2$ (2 degrees of freedom and 1 degree of freedom)

These corneal parameters may be altered or expanded upon in various ways. For example, goodness of fit may be extended to include fit information from each local measurement. Or, eccentricity and decentration information may be used to produce a more sophisticated correction for the central "k" measurement.

A few general comments are in order. First of all, it should again be stressed that the mathematical analysis is based on the assumption that the corneal axis is closer to the visual axis than are the peripheral sampling areas. This requirement is adequately satisfied for corneal axis within 1 mm of the visual axis, and the literature indicates the vast majority of corneas will satisfy this condition. For those corneas which have excessive decentration, there are several possible courses of action. One possibility is to merely indicate the excessive decentration as a factor of interest in itself and omit those computations which are most sensitive to the decentration. However, it should be noted that only statistically significant decentrations need be dealt with in this way. For example, a near spherical cornea has a very poorly defined corneal axis which can easily appear to be excessively decentered, but many of the calculations remain valid because the corrections implied for near spherical corneas are so small that the amount of corneal decentration is not very material.

Another possibility is to reformulate the mathematics based on the best estimate of the corneal apex position and recompute the corneal parameter, iterating until a consistent set of parameters is achieved. This iteration process may involve corrections to the local corneal measurement data $(x_i)$, particularly for unsymmetric corneal sampling arrays. This approach to the problem is manageable but computationally time-consuming and will not be dealt with here.

Referring to FIG. 11, the use of my invention in the fitting of contact lenses is schematically illustrated.

First, and as to eye E, successive measurements of the temporal, central and nasal portions of the cornea are taken. Once these successive measurements are taken, they are individually determined in accordance with the previous disclosure as represented by block 400. Thereafter, the results are typically processed for fitting as indicated at block 402 and forwarded to a map of the eye in the form of the parameters illustrated, the map being shown at block 403. Results of the map of the eye are passed to a data bank 404 where the map is retained.

Simultaneously with this measure, a contact lens empirically fitted to the eye E is removed and conventionally measured. These parameters of the contact lens are thereafter placed to the data bank. Measurement of the contact lens could of course occur by use of the individual keratometer.

It is important to note that the eye map and the contact lens dimensions constitute paired and corresponding data entries. These paired and corresponding data entries can be indexed in any convenient pattern desired so that upon location of similar and like eye maps, the appropriate contact lens can be called for.

Use of my eye measurement technique should at this point be apparent. Specifically, by mapping an eye, and making reference to a loaded data bank, a good estimate of those parameters necessary for a proper eye fit can be made.

I have previously noted that on the filing of this application, the mapping of eyes and the entry of a fitted contact lens into the data bank is simultaneous. Therefore, it may be expected that for similar maps, similar lens applications may result. At a minimum, I expect to be able to prescribe with much greater accuracy contact lenses.

It will be understood that there can be expected other parameters developed for the fitting of contact lenses as a result of the vastly more detailed corneal map which I have created. This will have to be recognized in the data as it develops. I file this application in advance of the accumulation of any such data.

I also contemplate as part of my invention the very important concept of taking corneal measurements over time spans. Specifically, it is known that the shape of the cornea can be effected by the presence of a contact lens upon it. Where the cornea undergoes shape alteration over a period of time because of the presence of a contact lens, it returns to a shape upon removal of the contact lens. It is important to remember that both the rate of return of the cornea to a shape upon removal of the contact lens as well as the shape to which the cornea returns can vary. For example, in orthokeratometry, the shape of the eye can conceivably be either permanently altered or temporarily altered dependent upon the characteristics of the contact lens used. With the measurements I disclosed taken over a time base, I clearly contemplate making measurements of the disclosed rates of return as well as the final state to which return occurs.

Referring to FIG. 11, it can be seen that the sphere, cylinder and axis results are plotted at specific time spans. For example, a first measurement is taken at 4:00. A second measurement is taken at 4:30. Likewise it will be apparent that additional time base measurements can be taken and the rates of change of corneal shape determined.

By way of illustration, I have shown a preferred map of the eye patterned after an elliptical model. It will be realized by those having skill in the art that other models exist by which the map I set forth may be predicted. What I have done is to set forth an apparatus and method whereby for the first time the enumerated factors of the eye may be rapidly obtained and practically used, not only to determine or monitor eye physiology but to insure enhanced fitting of contact lenses.

Regarding the time-base measurement which I have set forth wherein the cornea changes shape after removal of a contact lens, the time-base should be fully understood. Specifically, I contemplate beginning the counting of any time rate from the instant a contact lens is removed. It is at that time that the cornea is relieved of forces that might hold it out of shape and placed under its own natural dynamics to change to a new shape.

It will be appreciated that the foregoing specification and disclosed apparatus and method can be modified. For example, infrared diodes and detectors do not necessarily have to be used. Likewise, other modifications may be made without departing from the spirit of the invention.

What is claimed is:

1. A process for determining the shape of the cornea of the eye comprising: fixating the eye along a line of sight for measuring the eye at a first fixation; measuring the eye relative to said first fixation to determine sphere, cylinder and axis; fixating the eye at a second fixation; measuring the eye relative to said second fixation in sphere, cylinder and axis; fixating the eye at a third fixation; measuring the eye relative to said third fixation in sphere, cylinder and axis; determining from a combination of at least a portion of each said measurements of sphere, cylinder and axis at least one of the following parameters: central "k" readings in sphere, cylinder and axis; corneal shape factor; corneal decentrations; fits of corneal measurement to an overall elliptical corneal shape; vault height; cap size; "k" readings transposed to the corneal apex.

2. The process of claim 1 and wherein the measurement of said eye relative to at least one said fixation is along the line of sight to the eye.

3. The process of claim 1 and wherein and at a second and later time interval the eye is fixated along a line of sight for measuring the eye at a fourth fixation; measuring the eye relative to said fourth fixation to determine sphere, cylinder and axis; fixating the eye at a fifth fixation; measuring the eye relative to said fifth fixation in sphere, cylinder and axis; fixating the eye at a sixth fixation; measuring the eye relative to said sixth fixation in sphere, cylinder and axis; determining from a combination of at least a portion of each said fourth, fifth and sixth measurements of sphere, cylinder and axis at least one of the following parameters: central "k" readings in sphere, cylinder and axis; corneal shape factor; corneal decentration; fits of corneal measurement to an overall elliptical corneal shape; vault height; cap size; "k" readings transposed to the corneal apex; and comparing with respect to time the change of said determined parameter with respect to said previously determined parameter.

4. The process of claim 1 and wherein at a second and third time interval the eye is fixated along a line of sight for measuring the eye at a fourth fixation; measuring the eye relative to said fourth fixation to determine sphere, cylinder and axis; utilizing said eye in said fourth fixation to determine an alteration in sphere, cylinder and axis.

5. Apparatus for determining the shape of an eye comprising means for generating a keratometric measurement in sphere, cylinder and axis fixed to an eye along a line of sight; first, second and third targets for providing optical fixation of an eye at first, second and third lines of sight; means for switching said fixation targets on to permit said eye to be fixated at differing angles during measurement of said eye in sphere, cylinder and axis; means for retaining the measurement of said eye at each fixation; means for determining from a combination of at least a portion of said measurements of sphere, cylinder and axis at each fixation at least one of the following parameters: central "k" readings in sphere, cylinder and axis; corneal shape factor; corneal decentration; fits of corneal measurement to an overall elliptical corneal shape; vault height; cap size; "k" readings transposed to the corneal apex.

* * * * *